United States Patent
Maxwell

(10) Patent No.: US 7,838,230 B2
(45) Date of Patent: Nov. 23, 2010

(54) ASSAY FOR MEASURING AN ENZYME'S CAPABILITY TO MODIFY SUPERCOIL TOPOLOGY OF NUCLEIC ACIDS AND MODULATORS

(75) Inventor: Anthony Maxwell, Norwich (GB)

(73) Assignee: Plant Bioscience Limited, Norwich, Norfolk (GB)

( * ) Notice: Subject to any disclaimer, the term of this patent is extended or adjusted under 35 U.S.C. 154(b) by 610 days.

(21) Appl. No.: 11/718,978

(22) PCT Filed: Nov. 10, 2005

(86) PCT No.: PCT/GB2005/004346
§ 371 (c)(1),
(2), (4) Date: May 9, 2007

(87) PCT Pub. No.: WO2006/051303
PCT Pub. Date: May 18, 2006

(65) Prior Publication Data
US 2008/0026388 A1    Jan. 31, 2008

(30) Foreign Application Priority Data
Nov. 11, 2004    (GB) ................... 0424953.8

(51) Int. Cl.
*C12Q 1/68* (2006.01)
*C07H 21/02* (2006.01)
*C12N 9/00* (2006.01)
(52) U.S. Cl. ............................ 435/6; 536/23.1; 435/183
(58) Field of Classification Search ...................... None
See application file for complete search history.

(56) References Cited

U.S. PATENT DOCUMENTS
5,998,152 A    12/1999    Lynch et al.

(Continued)

FOREIGN PATENT DOCUMENTS
JP    59106292 A2    6/1984

(Continued)

OTHER PUBLICATIONS
Arimondo et al. (1999) C.R. Acad. Sci. Paris Life Sciences vol. 322 pp. 785-790.*

(Continued)

*Primary Examiner*—Samuel Woolwine
(74) *Attorney, Agent, or Firm*—Janet Sleath; Speckman Law Group PLLC

(57) ABSTRACT

Provided are methods, such as high throughput methods, of assessing or measuring the ability of an enzyme to modify the topology (e.g. supercoil topology) of a target nucleic acid, the methods comprising the steps of: (a) providing a solid support to which a capture nucleic acid is or may be immobilized, which capture nucleic acid is capable of binding the target nucleic acid in a manner that is proportional to the supercoil topology of said target nucleic acid (e.g. by triplex formation); (b) incubating a test mixture comprising (i) the enzyme, (ii) the target nucleic acid, (iii) capture nucleic acid, in the presence of (iv) said solid support, such that supercoiled target nucleic acid bound by the capture nucleic acid is immobilized to the solid support, (c) determining the amount of target nucleic acid bound by said capture nucleic acid in step (b) e.g. by use of a detectable label. The method may be used to screen for modulators of the enzyme activity.

27 Claims, 26 Drawing Sheets

U.S. PATENT DOCUMENTS

| | | |
|---|---|---|
| 6,197,527 B1 | 3/2001 | Lynch et al. |
| 6,620,588 B1 | 9/2003 | Bushman et al. |
| 2002/0173480 A1 | 11/2002 | Erikson et al. |
| 2004/0023207 A1* | 2/2004 | Polansky .................. 435/5 |

FOREIGN PATENT DOCUMENTS

| | | |
|---|---|---|
| WO | 99/23244 A1 | 5/1999 |
| WO | 99/27131 A2 | 6/1999 |
| WO | 99/46595 A1 | 9/1999 |
| WO | 99/49077 A1 | 9/1999 |
| WO | 01/98540 A2 | 12/2001 |
| WO | 02/04655 A2 | 1/2002 |
| WO | 03/012124 A2 | 2/2003 |
| WO | 04/083365 A2 | 9/2004 |
| WO | 04/087963 A1 | 10/2004 |

OTHER PUBLICATIONS

J. Biol. Chem., vol. 271, 1996, M Ivanchenko et al, "H1 binding unwinds DNA", 32580-32585.

Kawabata Y et al. Self-assembled plasmid DNA network prepared through both triplex-helix formation and streptavidin-biotin interaction. Macromol. Biosci. 2002, 2, 195-198.

Arimondo, Paola B. et al, "Targeting Topoisomerase I Cleavage to Specific Sequences of DNA by Triple Helix-Forming Oligonucleotide Conjugates. A Comparison Between a Rebeccamycin Derivative and Camptothecin," C.R. Acad. Sci. Paris, Sciences de la vie, vol. 322, pp. 785-790 (1999).

Arimondo, Paola B. et al, "Triple Helix-Forming Oligonucleotide Conjugated to Indolocarbazole Poisons Direct Topoisomerase I-Mediated DNA Cleavage to a Specific Site," Bioconjugate Chem., vol. 12, pp. 501-509 (2001).

Arimondo, Paola B. et al, "Design and Optimization of Camptothecin Conjugates of Triple Helix-Forming Oligonucleotides for Sequence-specific DNA Cleavage by Topoisomerase I," Journal of Biological Chemistry, vol. 277, No. 5, pp. 3132-3140 (2002).

* cited by examiner (a). Triplex formation between plasmid and immobilised complementary oligonucleotide (b). Capture of labeled oligonucleotide by triplex formation with plasmid and immobilized complementary oligonucleotide Surface of streptavidin-coated microplate Graph 1

Graph 2

Graph 3

Graph 4

Graph 5

Graph 6

Graph 7

Graph 8

Graph 9

Graph 10

Graph 11

Graph 12

Graph 13

Graph 14

Graph 15

Graph 16

Graph 17
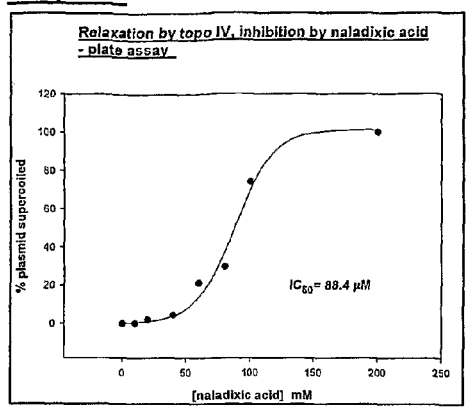
Graph 18
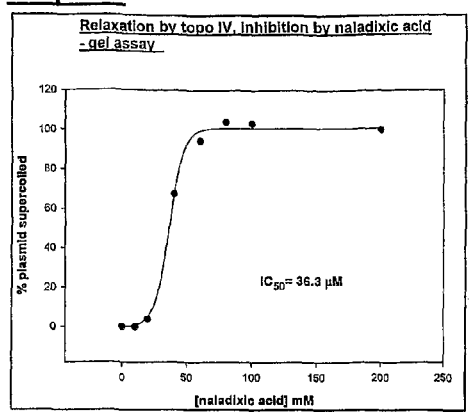
Graph 19
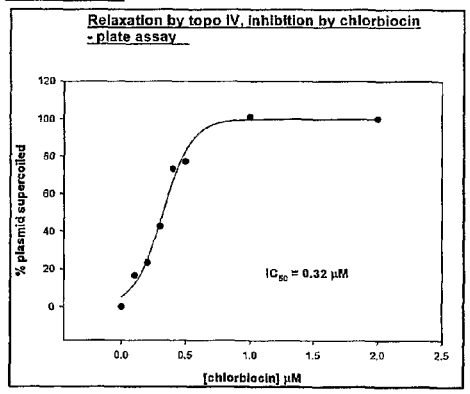
Graph 20
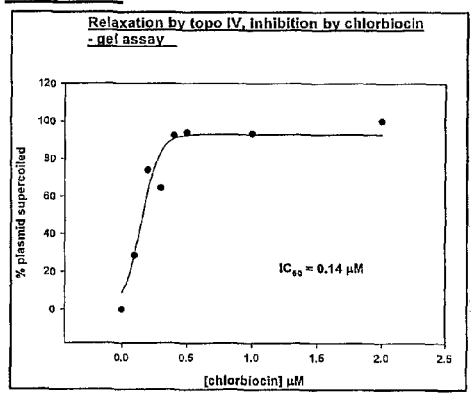
Figure 12 cont./

Graph 21

Graph 22

Graph 23

Graph 24

Graph 25

Graph 26

US 7,838,230 B2

SEQUENCE LISTING

<160> NUMBER OF SEQ ID NOS: 6

<210> SEQ ID NO 1
<211> LENGTH: 16
<212> TYPE: DNA
<213> ORGANISM: Artificial sequence
<220> FEATURE:
<223> OTHER INFORMATION: Triplex-forming oligonucleotide TFO1

<400> SEQUENCE: 1
tctctctctc tctctc         16

```
<210> SEQ ID NO 2
<211> LENGTH: 16
<212> TYPE: DNA
<213> ORGANISM: Artificial sequence
<220> FEATURE:
<223> OTHER INFORMATION: Triplex-forming oligonucleotide TFO2

<400> SEQUENCE: 2
ttcttcttct tcttct                                                       16

<210> SEQ ID NO 3
<211> LENGTH: 20
<212> TYPE: DNA
<213> ORGANISM: Artificial sequence
<220> FEATURE:
<223> OTHER INFORMATION: Triplex-forming oligonucleotide TFO1W

<400> SEQUENCE: 3
tcggagagag agagagagag                                                   20

<210> SEQ ID NO 4
<211> LENGTH: 20
<212> TYPE: DNA
<213> ORGANISM: Artificial sequence
<220> FEATURE:
<223> OTHER INFORMATION: Triplex-forming oligonucleotide TFO1C

<400> SEQUENCE: 4
ccgactctct ctctctctct                                                   20

<210> SEQ ID NO 5
<211> LENGTH: 20
<212> TYPE: DNA
<213> ORGANISM: Artificial sequence
<220> FEATURE:
<223> OTHER INFORMATION: Triplex-forming oligonucleotide TFO2W

<400> SEQUENCE: 5
aagaagaaga agaagaacgt                                                   20

<210> SEQ ID NO 6
<211> LENGTH: 20
<212> TYPE: DNA
<213> ORGANISM: Artificial sequence
<220> FEATURE:
<223> OTHER INFORMATION: Triplex-forming oligonucleotide TFO2C

<400> SEQUENCE: 6
tcttcttctt cttcttacgt                                                   20
```

ASSAY FOR MEASURING AN ENZYME'S CAPABILITY TO MODIFY SUPERCOIL TOPOLOGY OF NUCLEIC ACIDS AND MODULATORS

FIELD OF THE INVENTION

This invention relates generally to methods and materials useful for assaying enzymes which modify the supercoiling of nucleic acids (e.g. topoisomerases) and modulators of the same, for example in high-throughput systems.

BACKGROUND OF THE INVENTION

This invention disclosure provides novel methods for measuring the activity, and modulation of the activity, of DNA topoisomerases, essential enzymes that control the topological state of DNA in cells. The methods of this invention are also useful for measuring the activity of other enzymes, which affect the topological state of DNA, which for example includes, but is not limited to, restriction enzymes.

In prokaryotes topoisomerases are targets of antibacterial agents. In eukaryotes they are anti-tumour drug targets and potential herbicide targets. All topoisomerases can relax supercoiled DNA, and DNA gyrase, present in bacteria, can also introduce supercoils into DNA. Despite being the target of some of the key anti-microbials and anti-cancer drugs in use today (e.g. ciprofloxacin, camptothecins), the basic reaction catalyzed by these enzymes, the inter-conversion of relaxed and supercoiled DNA, is not readily monitored.

The standard assay for monitoring the superhelical state of nucleic acids is an electrophoresis gel-based assay, which suffers from the drawback of being slow and, due to the electrophoresis step, requires a lot of sample handling.

In response to this limitation, efforts have been made in recent years to develop high-throughput assays for topoisomerases. Reference is made here, for example, to U.S. Pat. No. 5,998,152, issued on Dec. 7, 1999, and U.S. Pat. No. 6,197,527, issued on Mar. 6, 2001, both issued to Tularik, and both of which are hereby incorporated by reference for the purpose of defining the background and state of the art defined therein. In the methodology according to those patents, a topoisomerase-nucleic acid complex is formed, denatured and identified, either in a solid-phase or liquid-phase format. Stabilization of a covalent complex between the protein and the DNA, and, in the solid-phase mode, immobilization of the enzyme, is required. In the liquid-phase assay, the signal is FRET between two labels on the DNA. That form of the Tularik assay nonetheless still relies on formation of a covalent cleavage complex, and, in this case, separation of the labels following cleavage. Thus, a limiting feature of the Tularik methodology is the requirement that a cleavable-complex, stabilized by a potential drug, must be formed. As such, these known assays are limited in their ability to identify only one mode of enzyme inhibitors. For example, such an assay would potentially identify a quinolone, but would not identify an aminocoumarin, such as novobiocin. Although the quinolone-type drugs are the most successful anti-topoisomerase agents currently available, it is not at all clear that appropriate non-quinolone inhibitors may not be just as effective, if not more so, were it possible to readily identify them. Accordingly, this is a drawback for the known Tularik high-throughput screening assays.

Accordingly, those skilled in the art will appreciate that there remains an interest in developing novel assays (such as high-throughput assays) to measure enzyme activities. Preferred assays would be generally applicable to identification of compounds with relevant topoisomerase or gyrase modulating efficacy. Such methodology would greatly facilitate work on topoisomerases (and other enzymes), and would specifically potentiate the use of combinatorial chemical libraries to screen for novel lead compounds (antibiotics, anti-tumour drugs, herbicides).

SUMMARY OF THE INVENTION

The methodology disclosed in the present patent disclosure seeks to address one or more of the limitations noted above in the known methods for assaying the activity of topology-modifying enzymes, such as the topoisomerases, gyrases and restriction enzymes.

Preferred embodiments may be capable of detecting any compound that inhibits the essential activity of these enzymes, and the present methodology is therefore in principle sensitive to all types of topoisomerase inhibitors. Likewise in preferred embodiments less enzyme may be required than in the prior art, and modification of the enzymes in the assay is not required. Additionally, in preferred embodiments, the invention utilises re-usable apparatus, which was not possible with certain prior art.

The invention provides, inter alia, methods of assessing or measuring the ability of an enzyme to modify the topology (e.g. supercoil topology) of a target nucleic acid. In other aspects it provides for methods for identifying compounds capable of modulating the activity of topoisomerases, gyrases and other enzymes which catalyze introduction or removal of supercoiling into nucleic acids includes detection of the degree of supercoiling of target nucleic acids in a format amenable to high-throughput screening of potentially modulating compounds. Preferred embodiments do not depend on the formation of a nucleic acid-enzyme covalent complex, and depend only on the initial state and final state of supercoiling of a target nucleic acid to provide information regarding the efficacy of test compound's ability to modulate the activity of the topoisomerase. The invention further provides kits useful for testing the topoisomerase or gyrase modulatory efficacy of a test compound, and compounds identified according to the methods of this invention.

Other objects and benefits of this invention will become apparent to those skilled in the art from a review of the full disclosure contained herein, and the claims appended to this disclosure.

DETAILED DESCRIPTION OF THE PREFERRED EMBODIMENTS

Figure 1:
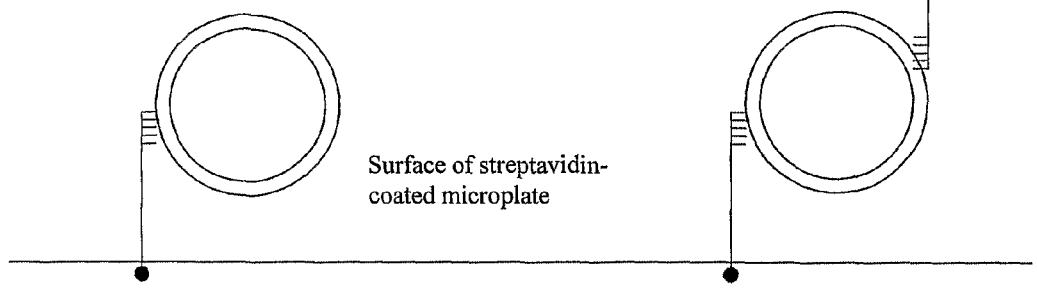
FIG. 1. Schematic representation of the two different embodiments of the high-throughput topoisomerase assay of this invention. An oligonucleotide (red) with a biotinylated 5'-end (black circle) is immobilized on a streptavidin surface (green). Due to its triplex-forming potential, this oligonucleotide can capture a supercoiled plasmid DNA molecule (blue). The plasmid can be detected directly using SYBR Gold (a), or indirectly using a second triplex-forming oligonucleotide with a fluorescent tag or radiolabel (asterisk).

In one aspect the invention provides a method of assessing or measuring the ability of an enzyme to modify the topology (e.g. supercoil topology) of a target nucleic acid, the method comprising the steps of:

(a) providing a solid support to which a capture nucleic acid is or may be immobilised, which capture nucleic acid is capable of binding the target nucleic acid in a manner that is proportional to the supercoil topology of said target nucleic acid;

(b) incubating a test mixture comprising (i) the enzyme, (ii) the target nucleic acid, (iii) capture nucleic acid, in the presence of (iv) said solid support, such that supercoiled target nucleic acid bound by the capture nucleic acid is immobilised to the solid support, (c) determining the amount of target nucleic acid bound by said capture nucleic acid in step (b).

The method, compositions and the kit adapted for carrying out the method, systems and compounds identified according to this invention, facilitate discovery of compounds capable of modulating the activity of topoisomerases or gyrases, without being limited to the mechanism by which such modulatory activity is achieved. This is accomplished by virtue of the current invention's focus, in a manner that is amenable to high-throughput screening, on the initial state and final state of supercoiling present in a target nucleic acid.

Various steps, procedures and compositions useful in carrying out the method are provided below, with further details being provided in the written description which follows. Those skilled in the art will appreciate that various steps of the method, while described discretely or in a particular sequence, may in some cases be carried out in a different sequence, concurrently, or not at all, depending on variations and modifications which are optional within the general scope of the method.

Some particular aspects and embodiments will now be discussed in more detail.

Preferably the capture nucleic acid is already immobilised to the solid support in step (a) i.e. prior to formation of the test mixture in step (b). Thus the method may comprise the step of immobilising the capture nucleic acid to the solid support in order to provide the solid support of step (a). The solid support may then be washed such as to minimise the amount of capture nucleic acid in the liquid phase in step (b).

In another embodiment the capture nucleic acid becomes immobilised to the solid support in step (b).

Step (b) may be carried out as two sub-steps. For example in a first sub-step a first pH may be selected which is optimal for, or conducive to, the activity of the enzyme, and results in modification of the supercoiling of the target substrate (e.g. pH 6 to 8). In a second sub-step a second pH may be selected which is optimal for, or conducive to, binding between the capture nucleic acid and target nucleic acid in a manner that is proportional to the supercoil topology of said target nucleic acid. Preferably the second pH will be lower than the first pH (e.g. less than pH 6).

Step (b) may optionally be followed by the step of washing the solid support to remove target nucleic acid which is not bound to the capture nucleic acid.

However where the invention is performed in a continuous flow context, such a washing step may not be required.

In step (c), preferably the amount of bound target nucleic acid is determined in situ on the solid support. This embodiment is particularly susceptible to detection by SPR or scanning of a nucleic acid chip or coated wells of a microplate. This may be carried out at a yet further pH to that or those used in step (b).

In another embodiment the bound target nucleic acid may be released from the capture nucleic acid (and hence solid support) and subsequently determined.

Immobilisation of the Capture Nucleic Acid

This may be via an immobilisation tag comprised within the capture nucleic acid e.g. biotin, which can combine with avidin present on the solid support. In this embodiment the immobilisation tag-capture nucleic acid combination forms an immobilisation moiety.

Streptavidin-coated microtiter plates are provided, to which the biotinylated oligonucleotides are bound (FIG. 1). Those skilled in the art will recognize that the mode by which the oligonucleotide is bound to the plate is a matter of experimental choice and preference, and that this mode of binding is exemplified here merely as a matter of convenience.

It will also be appreciated that while one exemplified mode of immobilizing a capture ligand, such as a triplex-forming oligonucleotide, may be based on avidin-streptavidin binding, or avidin-biotin binding, other modes of immobilizing the ligand may likewise be used. Antibody-antigen binding, covalent bonding and the like are all modifications that may be used with success to achieve the detection of DNA topology modification that forms the heart of this invention.

The Enzyme

The method may be used to assess the nucleic acid supercoiling or relaxing activity of any enzyme for which a substrate (target) nucleic acid can be provided—see e.g. U.S. Pat. No. 5,998,152, issued on Dec. 7, 1999, and U.S. Pat. No. 6,197,527, issued on Mar. 6, 2001. Preferably the enzyme is selected from topology-modifying enzymes, such as the topoisomerases, gyrases, nucleases restriction enzymes.

The Target Nucleic Acid

Depending on the enzyme activity which it is intended to assay, the target nucleic acid may be relaxed, supercoiled, or partially supercoiled at commencement of the assay, The target nucleic acid may be any nucleic acid but will be able to form a duplex and will generally be double stranded e.g. a double-stranded plasmid. It can be selected by those skilled in the art on the basis of the disclosure herein such that (a) its supercoil topology can be modified by an enzyme it is desired to assay, and (b) it contains at least one region or insert capable of forming a triplex with the capture nucleic acid.

Those skilled in the art will appreciate that the nucleic acid utilized as a substrate for the enzyme whose activity is being tested (optionally for modulation by potential enzyme modulating compounds—see below) may be in any appropriate form for the enzymatic activity at issue. Thus, for determining the modulatory activity of a potential topoisomerase or gyrase enzyme, the target nucleic acid is preferably a closed-circular segment of DNA. While the size of such a closed-circular target DNA is not critical per se, it is desirable for the size to be sufficient to permit an appreciable difference between supercoiling and non-supercoiling to be detectable by, for example conventional gel-electrophoretic means.

While plasmid DNA is convenient for use as the target nucleic acid substrate according to the method of this invention, those skilled in the art will appreciate that other forms of DNA may be conveniently utilized as well. Thus, for example, a linear DNA tethered at both ends, and thus forming a closed domain, could be used in the assay.

For high-throughput quantitation of the modulatory activity of test compounds (see below) where the subject enzymatic activity is that of a restriction enzyme, the DNA substrate will be a supercoiled plasmid, which will be linearised upon treatment with the enzyme. In this case the substrate will bind the triplex and be detected whereas the product (linear DNA) will not.

In one embodiment the triplex forming insert comprises pyrimidine rich and purine rich sequences i.e. sequences which contain a contiguous sequence of equal to, or at least, 10, 15 or 20 pyrimidines or purines respectively.

Optionally these sequences may contain a contiguous sequence of at least 5, 7 or 10 alternating pyrimidine or purine repeats respectively e.g. AG or TC repeats.

Optionally these sequences may contain a contiguous sequence of at least 3, 5 or 7 triplets e.g. AGA, AAG, GAA, GAG, GGA, AGG (purines) or e.g. TCT, TTC, CTT, CTC, CCT, TCC (pyrimidines).

Optionally the sequences are selected from any of TF01W; TF01C; TFO2W; TFO2C described herein, or is at least 80% identical thereto.

The Capture Nucleic Acid

The capture nucleic acid will not be a substrate for the enzyme.

The capture nucleic acid utilized for triplex formation need not be composed of canonical oligonucleotides. It may include modified bases, for example inosine, and may have modified backbones, for example, a PNA (Peptide Nucleic Acid) may be utilized in the assay. Peptide Nucleic Acid (PNA) is an analogue of DNA in which the backbone is a pseudopeptide rather than a sugar. PNA mimics the behaviour of DNA and binds complementary nucleic acid strands. The neutral backbone of PNA can result in stronger binding and greater specificity than may otherwise be achieved.

The capture nucleic acid binds the target nucleic acid in a manner that is proportional to its supercoiling. For example the capture nucleic acid is capable of preferentially forming a triplex with supercoiled (e.g. negatively supercoiled) target nucleic acid compared with relaxed target nucleic acid.

In one preferred embodiment of the present invention, preferential formation of inter-molecular DNA triplexes in supercoiled, as compared with relaxed, plasmid DNA, is utilized to immobilize nucleic acid which serves as a substrate for the enzyme of interest. Without wishing to be bound by theory or mechanism, it has now generally been accepted in the art that the greater the degree of supercoiling in a segment of DNA, the greater the exposure of the major groove in that segment of DNA, and the greater the degree of access to specific sequences present in the DNA to sequence specific ligands contacted with the DNA. Thus, an oligonucleotide containing a specific sequence complementary to a sequence present in the target nucleic acid can be used as the immobilization moiety, and the specific complementary sequence can act as the nucleic acid binding moiety. If the target nucleic acid is duplex in nature, then a triplex is formed between the oligonucleotide and target nucleic acid, under the appropriate incubation conditions. Such conditions are readily definable by those skilled in the art, based on the specific sequence composition—see e.g. US publication 2002/0173480 or Kawabata, Y., Ooya, T., Lee, W. K. and Yui, N. (2002) Self-assembled plasmid DNA network prepared through both triple-helix formation and streptavidin-biotin interaction. *Macromol Biosci,* 2, 195-198.

In one embodiment the capture nucleic acid may be pyrimidine rich such as to bind parallel to a purine-rich strand of the target nucleic acid (or vice versa).

In one embodiment the capture nucleic acid may be pyrimidine rich i.e. contain a contiguous sequence of equal to, or at least, 10, 15 or 20 pyrimidines—preferably the pyrimidines are T and C.

Preferably the capture sequence contains a contiguous sequence of at least 5, 7 or 10 alternating pyrimidine repeats e.g. TC repeats.

Optionally the capture sequence may contain a contiguous sequence of at least 3, 5 or 7 triplets e.g. TCT, TTC, CTT, CTC, CCT, TCC.

Optionally the capture sequence is selected from TFO1 or TFO2 described herein, or is at least 80% identical thereto.

We have shown that supercoiled plasmid DNA molecules are captured more efficiently than their relaxed counterparts (see the Examples).

Thus immobilised oligonucleotides may be used to capture a DNA duplex by triplex formation, under appropriate reaction conditions, analogous to those set forth below in the experimental section. Appropriate reaction conditions may be defined by those skilled in the art, based on the teaching disclosed herein, without undue experimentation, for any particular set of oligonucleotide ligand-target DNA combinations. Likewise for any other DNA-supercoil status-dependent ligand that is chosen for use in a particular application or system, if it is determined that, consistent with the teachings of this invention, it is preferable to use a mode of supercoil status detection other than triplex formation.

Particular preferred capture and target nucleic acid combinations or identities are discussed further in respect to kits of the invention below.

The Determination Step and Solid Support

Optionally the amount of bound nucleic acid may be determined by use of labelling moiety which is or includes a detectable label, such as a fluorescent dye, or radiolabel.

This may be one which is present on, or incorporated into, the target nucleic acid.

In an embodiment of this invention adapted for high-throughput screening of topoisomerase modulatory compounds (see below) reference is conveniently made to FIG. 1(a), in which detection of captured plasmid DNA is direct, using, for example in a non-limiting sense, a commercially available nucleic acid stain, such as SYBR® Gold dye (a commercially available but proprietary unsymmetrical cyanine dye that exhibits greater than 1000-fold fluorescence enhancement upon binding nucleic acid; available from Molecular Probes, Inc.,) and a florescence microplate reader. Because of the significant degree of fluorescence enhancement achieved with this reagent, it may not be necessary for achievement of acceptable signal to noise ratios to even wash away any unbound labelling moiety, making such a washing step unnecessary in the method of this invention.

In a further direct method of detection, the plasmid nucleic acid itself may be detectably labelled in a manner that does not interfere with the relaxation or supercoiling of the DNA. Thus, the nucleic acid may be radioactively labelled by incorporation of, for example, radioactive phosphorous (e.g. $^{32}P$), or a fluorescent moiety that is incorporated into the nucleic acid. In this event, addition of a separate labelling moiety is optional, and washing of unbound nucleic acid is sufficient to permit a direct readout as to the degree of enzyme activity modulation that has been achieved.

In another embodiment, the detectable label may be bound to the target nucleic acid or target nucleic acid-capture nucleic acid complex in situ. In such embodiments there may be a wash step to remove unbound labelling moiety.

Alternatively the moiety may be bound to the target nucleic acid after its release from the solid support—for example the labelling moiety may be a nucleic acid capable of forming a triplex with the supercoiled (e.g. negatively supercoiled) target.

Thus in another embodiment according to this invention, detection of the captured DNA may be indirect. Thus, for example, referring to FIG. 1(b), a second triplex-forming oligonucleotide bearing a fluorescent tag, a radiolabel, or other detectable tag may be used. Likewise, a ligand other than an oligonucleotide may be used, consistent with the teachings provided herein, should this be necessary or desirable for a given application. Where a second, labelled nucleic acid is used, it is important that the second oligonucleotide is designed so as to bind to a different portion of the target nucleic acid, to ensure that the triplex formed between the second oligonucleotide and the target plasmid DNA does not compete with triplex formation between the first immobilization oligonucleotide or moiety. The second oligonucleotide or detection moiety may be fluorescently labelled, radioactively labelled, or labelled in any other manner that is convenient and amenable to easy detection, and preferably, high-throughput screening of target compounds. Whether applied according to FIG. 1(a) or (b), those skilled in the art will appreciate certain benefits of this invention.

The solid support may be adapted to facilitate detection e.g. a multi-well plate which can be interrogated by a fluorimeter or radioactivity detector. In other continuous flow embodiments the solid phase may be a glass capillary, flow cell, or the surface of a wave guide (e.g. for detection by SPR, the 'chip' or flow cell of a Biacore™ sensor.)

Those skilled in the art will recognize, in light of the specific teachings provided herein, that various modifications may be made to the invention without departing from the central aspect thereof defined according to the claims below. Thus, for example, those skilled in the art will appreciate that methods of signal amplification may be applied to this invention to maximize the signal-to-noise ratio, to increase the sensitivity or detection-limit of the method, and to reduce the amount of reagents used in the method. Thus, for example, in one form of signal amplification, to a first ligand bound to nucleic acid immobilized according to this method, multiple ligands each bearing their own detectable signal may be bound. It will also be appreciated that the detection method is not restricted. Thus, fluorescent labels or dyes, radiolabel signals and appropriate modes of detection may all be modified according to the needs of a particular application.

Screening for Modulators

In one aspect of this invention, a method is provided for measuring the activity of an enzyme (e.g. topoisomerase or gyrase) in the presence of a potential enzyme activity modulator.

Any of the preferred embodiments discussed hereinbefore are also applicable to these aspects of the invention.

Thus in a further aspect the invention provides a method of assessing or measuring the modulating activity of a potential modulator on the ability of an enzyme to modify the topology (e.g. supercoil topology) of a target nucleic acid, the method comprising the steps of:

(a) providing a solid support to which a capture nucleic acid is or may be immobilised, which capture nucleic acid is capable of binding the target nucleic acid in a manner that is proportional to the supercoil topology of said target nucleic acid;

(b) incubating a test mixture comprising (i) the enzyme, (ii) the target nucleic acid, (iii) capture nucleic acid, in the presence of (iv) said solid support and (v) the potential modulator, such that supercoiled target nucleic acid bound by the capture nucleic acid is immobilised to the solid support, (c) determining the amount of target nucleic acid bound by said capture nucleic acid in step (b).

Optionally the value resulting from the determination at step (c) (i.e. obtained in the presence of modulator) is compared with the value in its absence, and the modulating activity is correlated with the result of the comparison.

Another aspect of the invention generally involves incubating a test mixture containing (i) an enzyme such as a topoisomerase or gyrase, (ii) a nucleic acid, optionally comprising a labelling moiety, and (iii) a potential activity modulator. To such a test mixture, (iv) an immobilization moiety is added which includes an immobilization tag and a nucleic acid binding moiety that binds the nucleic acid in a manner that is proportional to the degree of supercoiling present in the nucleic acid. The immobilization tag may already be bound to a solid support, and the test mixture may be added to the solid support to which is bound the immobilization moiety, or the entire mixture may be concurrently created in a solid support, such as a well of a microtiter dish. In any event, regardless of the exact sequence chosen, the immobilization tag is bound to (v) a solid support, thereby binding the immobilization moiety to the solid support. Any nucleic acid bound to the immobilization moiety via the nucleic acid binding moiety present on the immobilization moiety is also thereby bound to the solid support. At this stage, preferably, the solid support is washed to remove nucleic acid which is not bound to the immobilization moiety. The solid support-bound immobilization moiety, and any nucleic acid bound to the immobilization moiety via the nucleic acid binding moiety, is contacted with (vi) a labelling moiety. This step may be unnecessary if a labelling moiety is already included in the nucleic acid utilized as the substrate for the test enzyme. Thus, for example, the nucleic acid may be fluorescently or radioactively labelled. In any event, any unbound labelling moiety, whether separately added or if contained within the nucleic acid itself, is washed away if necessary, under conditions which do not disrupt the immobilization of the nucleic acid which is bound to the immobilization moiety. Ultimately, the goal of the method is achieved by determining whether, and if quantitative data is required, to what degree, a potential topoisomerase or gyrase activity modulator included in the method in fact modulates the activity of the topoisomerase or gyrase. This is achieved by measuring the degree of nucleic acid bound to the immobilization moiety, for example by measuring the amount of labelling moiety bound to the solid support following washing, or the amount released therefrom after the wash step is complete. A control is generally set up in which all of the foregoing elements apply, but the test compound is not included in the mixture.

While triplex formation (as described above) is identified as a preferred mode of carrying out the method of this invention, any immobilizable ligand which preferentially binds to a target nucleic acid in a manner that is proportional to the degree of supercoiling in the DNA would suffice. Thus, for example, it is known that the *E. coli* histone-like protein Huα preferentially binds to negatively supercoiled DNA, (Shindo, et al., 1992, Nuc. Acids Res. 20(7), 1533-1558) and thus, this protein, or a portion thereof may be used as a ligand according to this invention. Likewise, histone proteins, or portions thereof, which retain the selectivity of histone binding to nucleic acids in different states of supercoiling, may be utilized according to this invention.

Antibodies to such proteins, as well as tagged antibodies, may likewise be utilized to advantage in the present method. Even the enzymes or portions of the enzymes whose activity is monitored herein may be utilized as ligands according to the method of this invention, provided that the enzymatic activity of the enzyme is deactivated, and the inclusion of the enzyme or portion thereof does not interfere with the activity of the target enzyme being monitored. Detection of the bound protein could be by antibody detection, coupling the protein to an enzyme whose activity can be monitored (e.g. luciferase), or any other known convenient detection system. For these modes of target nucleic acid binding, known sequence-specific and/or conformation specific determinants of nucleic acid binding are optimized to ensure that the degree of ligand binding is proportional to the degree of supercoiling.

While a wide variety of methods may be used for immobilizing oligonucleotide ligands, in one exemplary embodiment of this aspect, the immobilization moiety is an oligonucleotide as discussed above. This may optionally be biotinylated to form an immobilization tag. Without wishing to be bound by mechanism, because of the ability to control specific sequence binding, and thus the ability to model a portion of DNA which will be exposed in the major groove of the DNA upon supercoiling, a preferred embodiment of the present invention utilizes the ability to form a triplex between a probe nucleic acid, such as an oligonucleotide, and the target nucleic acid acted on as a substrate by the topoisomerase.

It will also be appreciated that the target DNA undergoing supercoiling or relaxation in the presence of the topoisomerase (and optionally test compound) may be the immobilized moiety, without departing from the essential methodology of the invention disclosed herein, and a detectable supercoil status dependent ligand, such as an oligonucleotide, may be added to the thus immobilized target nucleic acid.

Those skilled in the art will appreciate, based on the teachings provided herein, that the methodology of this invention is not limited to detection of compounds having topoisomerase modulatory activity. The methodology of this invention is amenable to evaluation of compounds having modulatory activities relevant to a variety of other enzymes, including nucleases and restriction enzymes. Thus, with respect to a restriction enzyme, activity of the enzyme on a supercoiled substrate will be detected according to the method of this invention, as the nucleic acid supercoiling is released when the supercoiled DNA is linearized by the restriction enzyme.

Those skilled in the art will also appreciate that other processes that modulate supercoiling, such as drug binding to DNA may likewise be monitored according to the method of this invention. The method of this invention is also carried out with catenated DNA as the substrate. In this case, a singly-linked catenane is formed in which one partner circle (ideally the smaller of the two) contains a triplex-forming sequence that is complementary to an immobilized ligand, such as the triplex-forming oligonucleotide. Treatment with a topoisomerase (generally topo II) releases the unattached circle. Staining with SYBR or other detection method reveals those samples in which a reaction has occurred, as a reduction in the amount of indicator proportionate to the reduced amount of DNA present following decatenation.

Thus it will be understood that in this embodiment of the invention, the invention provides a method of assessing or measuring the ability of an enzyme to modify the topology of a target nucleic acid (by decatenation thereof), the method comprising the steps of:

(a) providing a solid support to which a capture nucleic acid is or may be immobilised, wherein the target nucleic acid is a concatenated closed circular plasmid DNA, and wherein the capture nucleic acid is capable of binding one of the circles of the target nucleic acid in a manner that is proportional to its supercoil topology;

(b) incubating a test mixture comprising (i) the enzyme, (ii) the target nucleic acid, (iii) capture nucleic acid, in the presence of (iv) said solid support, such that supercoiled target nucleic acid bound by the capture nucleic acid is immobilised to the solid support, (c) determining the amount of target nucleic acid bound by said capture nucleic acid in step (b).

The release of that portion of the target nucleic which is not bound in a manner that is proportional to the supercoil topology (e.g. the larger circle, which does not itself contain a triplex forming sequence) means proportionally less target nucleic acid is bound, and this can be detected by staining.

For academic research, the method according to this invention provides enhanced ability to analyze topoisomerase reactions more rapidly and more quantitatively, and facilitates rapid evaluation of potential inhibitors/toxins. For purposes of targeted drug development, the method according to this invention enables rapid assay of compound libraries in a high-throughput format, without limiting the potential drug candidates to a particular mode or mechanism of activity.

The invention further provides modulators identified or identifiable in accordance with the methods herein, and use of the same for modifying the activity of the enzymes discussed herein. Thus the invention provides for:

(a) identifying a compound which has the ability of modulate the activity of an enzyme to modify the supercoil topology of a target nucleic acid, (a) producing said compound e.g. preparing it as a medicament or drug.

Kits

The invention further provides kits, for example including solid phase with capture nucleic acid (and optionally target nucleic acid) immobilised thereto; vials of substrate (target nucleic acid) in various different degrees of supercoiling; buffers etc.

For example a kit may provide:

(a) a capture nucleic as discussed herein, (b) a target nucleic acid as discussed herein. and optionally one or more of:

(c) a solid phase, (d) one or more buffers for performing one or more steps of the invention, (e) printed instructions for use of the methods of the invention.

In one aspect of this invention, a kit is provided wherein an optimized oligonucleotide having a sequence which matches a particular sequence in a target, closed-circular DNA is provided. In that embodiment of the invention, the conditions for interaction of the oligonucleotide in triplex formation with the closed-circular DNA have been optimized for high-throughput screening of potentially modulatory compounds. For purposes of such a system and test kit, the size of the DNA has been found to be adequate when a closed circular DNA of between about 0.1 kb and 10 kb is utilized. Practically speaking, however, where quantities of the target DNA are to be generated, inclusion of an origin of replication, selectable drug resistance markers, and the like, tend to mean that in general, a plasmid DNA molecule easily produced in bulk in bacteria in a size of about 1 kb to about 5 kb will be generally utilized. Those skilled in the art will appreciate that stocks of plasmid DNA for use according to this invention may be conveniently produced by transformation of a suitable bacterial host with a plasmid DNA containing appropriate replication signals contained therein, and harvesting the plasmid DNA according to methods now well established and known in the art.

In a preferred embodiment of this invention, the test kit comprises an oligonucleotide and a target nucleic acid, wherein the oligonucleotide and target nucleic acid interaction for triplex formation has been optimized under standard assay conditions. In this manner, those wishing to conduct the method of this invention are facilitated by having available a known system according to this invention in which, under standard assay conditions, efficacy of test compounds and specific topoisomerases, gyrases, restriction enzymes and other enzymes that modulate the supercoil topology of nucleic acids may be ascertained.

These and other aspects of this invention are outlined in the claims which follow and which provide, including equivalents thereof, the proper measure of the invention defined herein.

EXAMPLES

Having generally described this invention with respect to its mode of operation, (including its best mode), those skilled in the art are provided the following exemplary disclosure to ensure that they are fully enabled to practice this invention, and that the written description thereof is fully adequate so as to advise those wishing to practice this invention of its many advantages, including its best mode. However, it should be understood that this invention is not limited in its scope to the specifics of this exemplary support. Reference is made for this purpose to the claims appended to this invention disclosure, including the equivalents thereof, as a definition of the scope of this invention.

Material and Methods

Unless indicated otherwise, the following materials and methods were used in the Examples which follow:

Enzymes, DNA and Drugs:

*Escherichia coli* DNA gyrase and DNA topoisomerase (topo) IV were from John Innes Enterprises Ltd. (gifts of Mrs. A. J. Howells); DNA topoisomerase I (wheat germ) was purchased from Promega. Restriction enzymes were purchased from New England BioLabs (AvaI and AatII) and Invitrogen (EcoRI). Triplex-forming oligonucleotides (TFOs) were purchased from Sigma Genosys and are listed in Table 1, Example 1 below. Plasmid pBR322* was from John Innes Enterprises Ltd. (gift of Mrs A. J. Howells). TFO2 was radiolabelled using polynucleotide kinase and $^{32}$P-dATP. Radiolabelled oligos were separated from unlabelled material using Microspin G-25 columns (Amersham Biosciences). Ciprofloxacin and novobiocin were purchased from Sigma and Fluka, respectively; SYBR Gold nucleic acid stain was purchased from Invitrogen.

The DNA substrate used (pNO1) contained a small amount of nicked (open circular) plasmid. The relaxed DNA consisted of a range of topoisomers which ran as a series of bands close to the nicked band.

Treatment of relaxed pNO1 with DNA gyrase converts the relaxed topoisomers to a single supercoiled band, with the nicked DNA band above. Conversely, treatment of supercoiled pNO1 with topoisomerase IV converts the single supercoiled band to a range of relaxed topoisomers.

Surface Plasmon Resonance (SPR):

SPR was carried out using a Biacore X instrument. Streptavidin-coated chips (SA chip; Biacore International SA) had ~5 µl 100 nM biotinylated oligo (TFO1 or TFO2) in HBS-EP Buffer (Biacore International SA) immobilised onto flow cell 2 (giving a response of ~250 RU). Plasmids in TF Buffer (50 mM sodium acetate (pH 5), 50 mM NaCl, 50 mM MgCl$_2$) were injected at a concentration of 4 nM. The SA chip was regenerated using 50 µl 1 M NaCl in 50 mM NaOH.

Gel Electrophoresis:

DNA gyrase supercoiling assays, using gel electrophoresis, were carried out based on published procedures as follows: Reactions (30 µl) contained 1 µg relaxed pBR322*, in 35 mM Tris.HCl (pH 7.5), 24 mM KCl, 4 mM MgCl$_2$, 2 mM dithiothreitol, 1.8 mM spermidine, 1 mM ATP, 6.5% (w/v) glycerol, 0.1 mg/ml albumin (John Innes Enterprises) and were incubated at 37° C. for 30 min. Samples were analysed on 1% agarose gels.

Enzyme Assays:

DNA gyrase supercoiling assays, using gel electrophoresis, were carried out based on published procedures as follows. Reactions (30 µl) contained 1 µg relaxed plasmid DNA, in 35 mM Tris.HCl (pH 7.5), 24 mM KCl, 4 mM $MgCl_2$, 2 mM dithiothreitol, 1.8 mM spermidine, 1 mM ATP, 6.5% (w/v) glycerol, 0.1 mg/ml albumin (John Innes Enterprises) and were incubated at 37° C. for 30 min. Samples were analysed either using microplate assays (below) or by electrophoresis on 1% agarose gels. Where indicated ciprofloxacin and novobiocin were also added to assays. Topo I and topo IV assays were carried out according to the manufacturer's instructions (Promega and John Innes Enterprises Ltd.) using 1 µg supercoiled plasmid DNA as substrate.

In all experiments, the activity of the enzyme was determined by titration, and 1 U defined as the amount of enzyme required to fully supercoil, or relax the substrate.

It was found that reducing the amount of BSA in the wash buffer (from 0.1% w/v BSA to 0.01% w/v BSA) did not give an observable difference in results. Therefore later assays (in Examples 5 onwards) were performed using the lower amount to reduce costs.

Example 1

Preparation of Test Nucleic Acid for Supercoil/Relaxation Testing:

To enable specific capture of plasmids by triplex formation with immobilised oligos, plasmids containing triplex-forming sequences were constructed. To construct plasmid pNO1, oligos TFO1W and TFO1C (Table 1) were annealed and ligated into the AvaI site of pBR322*. To construct plasmid pNO11, oligos TFO2W and TFO2C (Table 1) were annealed and ligated into the AatII site of pNO1. The sequences of pNO1 and pNO11 were verified by DNA sequencing. Supercoiled forms of plasmids were prepared by transforming them into Top10 competent cells (Invitrogen) and growing in LB broth containing ampicillin (Sigma), and preparing the DNA using Qiagen mini and midi prep kits. Relaxed plasmids were prepared by incubating the supercoiled forms with topo I (~40-50 µg plasmid, 200 units topo I, in 50 mM Tris.HCl (pH 7.5), 50 mM NaCl, 0.1 mM EDTA), for 1 h at 37° C. Relaxed plasmids were purified by phenol/chloroform extraction and ethanol precipitation. 'Half-supercoiled' plasmids were made by relaxing the supercoiled form (42 µg) with topo I in the presence of 1.1 µg/mL ethidium bromide in a total volume of 1 mL.

TABLE 1

| SEQ. ID. No. | Name  | Sequence (5'-3')       | 5' modification        |
|--------------|-------|------------------------|------------------------|
| 1            | TFO1  | TCTCTCTCTCTCTCTC       | Biotin                 |
| 2            | TFO2  | TTCTTCTTCTTCTTCT       | Biotin or $^{32}P$     |
| 3            | TFO1W | TCGGAGAGAGAGAGAGAGAG   |                        |
| 4            | TFO1C | CCGACTCTCTCTCTCTCT     |                        |
| 5            | TFO2W | AAGAAGAAGAAGAAGAACGT   |                        |
| 6            | TFO2C | TCTTCTTCTTCTTCTTACGT   |                        |

Plasmid pNO1 is a modified form of pBR322 containing a 20 bp insert with triplex-forming potential; pNO11 is a modified form of pNO1 containing a second 20 bp insert with triplex-forming potential. The first triplex-forming insertion, in both pNO1 and pNO11, should allow them to be captured by biotinylated oligo TFO1 (Table 1). The second triplex forming insertion, in pNO11, should allow a second triplex formation with TFO2, which is end-labelled for quantitation. The pyrimidine-rich TFO1 and TFO2 oligos should form triplexes in the major grove of the inserted sequences in pNO1 and pNO11, binding parallel to the purine strand, forming $C^+.GC$ and T.AT triplets. In control experiments, we showed that both plasmids can be relaxed by topo I, and that the relaxed form can be supercoiled by DNA gyrase (data not shown).

Example 2

Figure 2A:
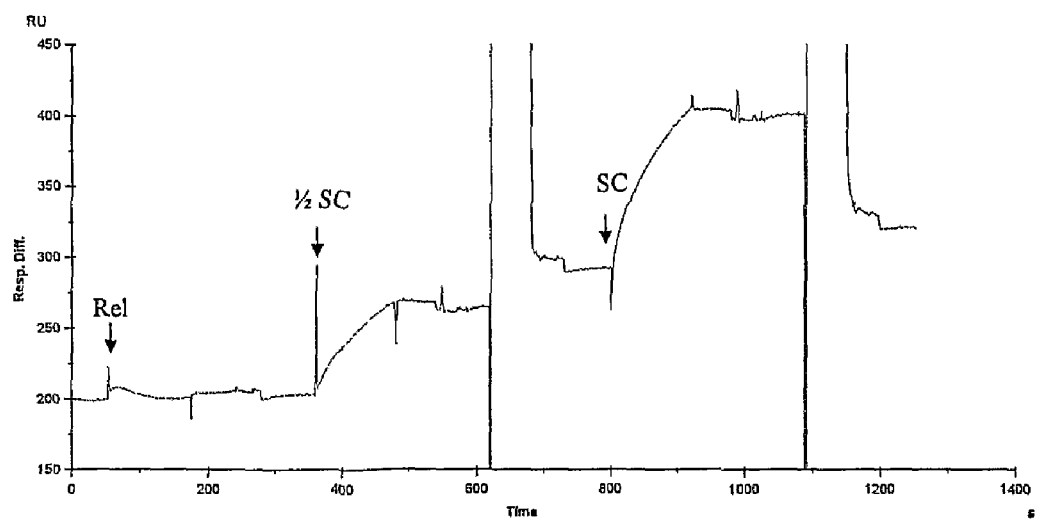
FIG. 2. Capture of plasmids by triplex-forming oligos using detection by SPR. Biotinylated oligos were immobilised on a streptavidin chip in a Biacore X instrument, and plasmids (4 nM) were flowed over the chip surface. A. Sensorgram showing capture of different forms of pNO1 by immobilised TFO1: Rel=relaxed, ½ SC=partially supercoiled, SC=supercoiled. B. Histogram of response for each of the forms of pNO1 in A. C. Capture of relaxed and supercoiled pNO11 by TFO1. D. Capture of relaxed and supercoiled pNO11 by TFO2.
Figure 2B:
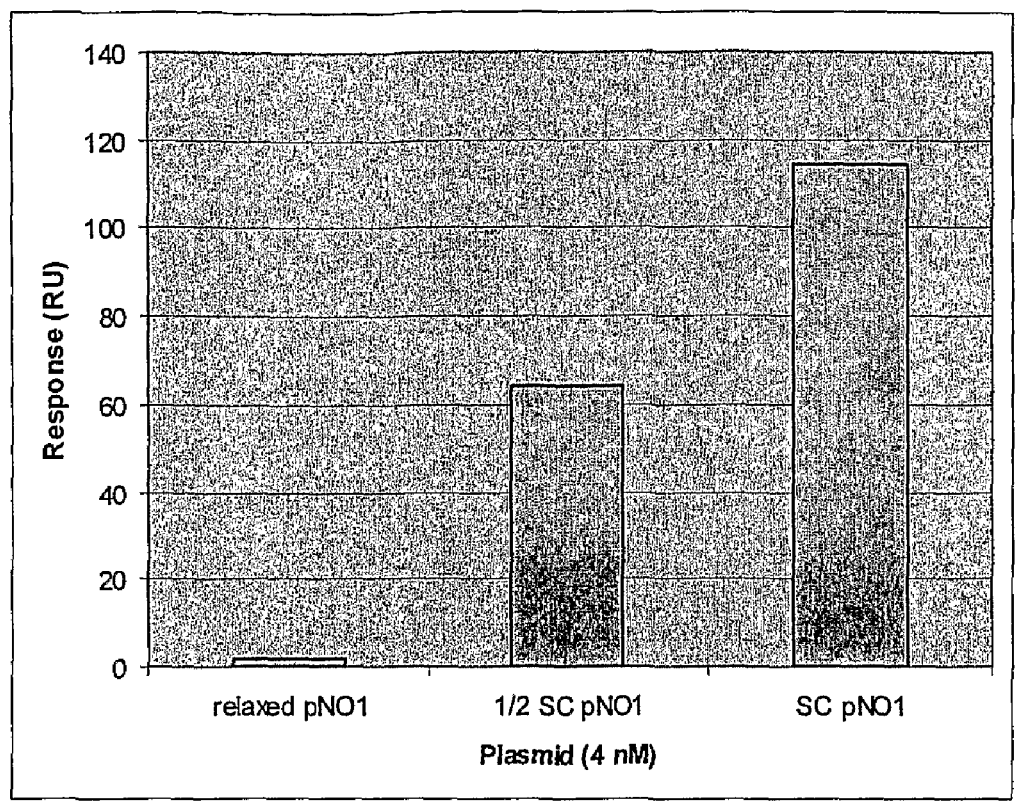

Surface Plasmon Resonance (SPR):

We used SPR to demonstrate plasmid capture by TFOs and to optimise conditions for triplex formation. The TFO was first immobilised onto one of two flow cells using a streptavidin-coated chip and a biotinylated oligo. The plasmid was then injected over the flow cells. Any bound plasmid was subsequently washed off to regenerate the chip. In control experiments we found that plasmids with multiple triplex-forming inserts were captured less efficiently than those with single inserts (data not shown). When the solution conditions were varied, we found that a metal ion was required ($MgCl_2$), salt was required (either NaCl or KCl) and that low pH is optimal (pH~5); the best buffer for triplex formation was found to be: 50 mM sodium acetate (pH 5), 50 mM NaCl and 50 mM MgCl2 (=TF Buffer). Under these conditions we evaluated the capture of negatively supercoiled, relaxed and partially supercoiled pNO1 by TFO1 (FIG. 2A,B). These experiments showed that supercoiled pNO1 was efficiently captured by comparison with its relaxed form; partially supercoiled pNO1 (specific linking difference ~0.03) gave a response approximately mid-way between the other two forms. In control experiments we found that supercoiled pBR322*, which has no triplex-forming inserts, was not captured (data not shown). We also showed that pNO1 could not be efficiently captured by TFO2 (data not shown).

Figure 2C:
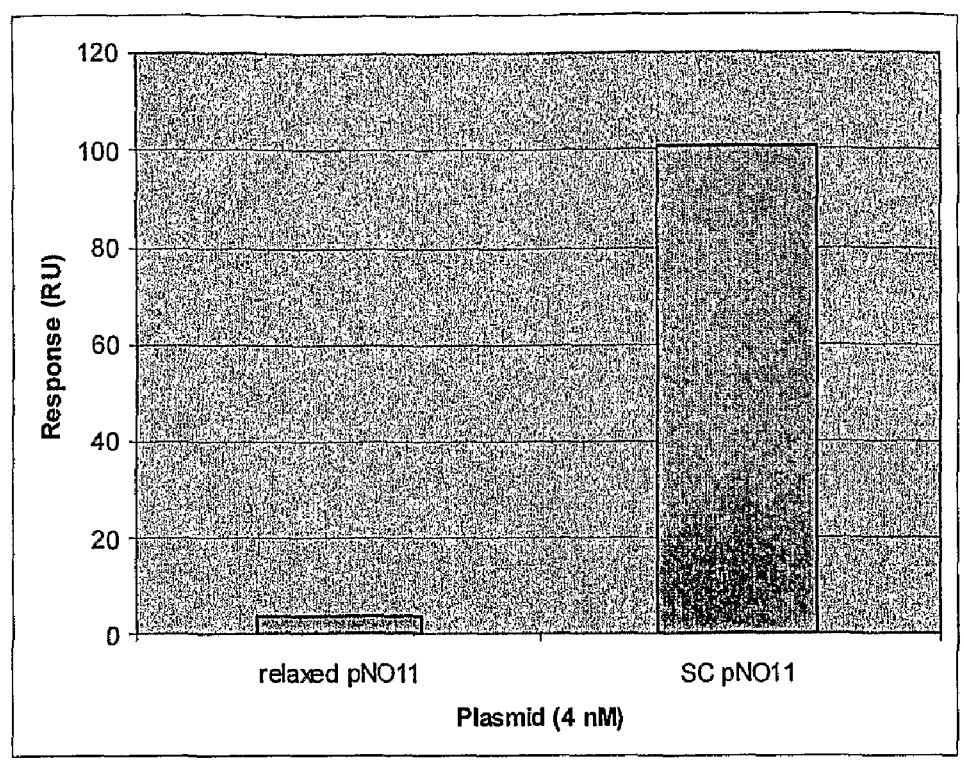
Figure 2D:
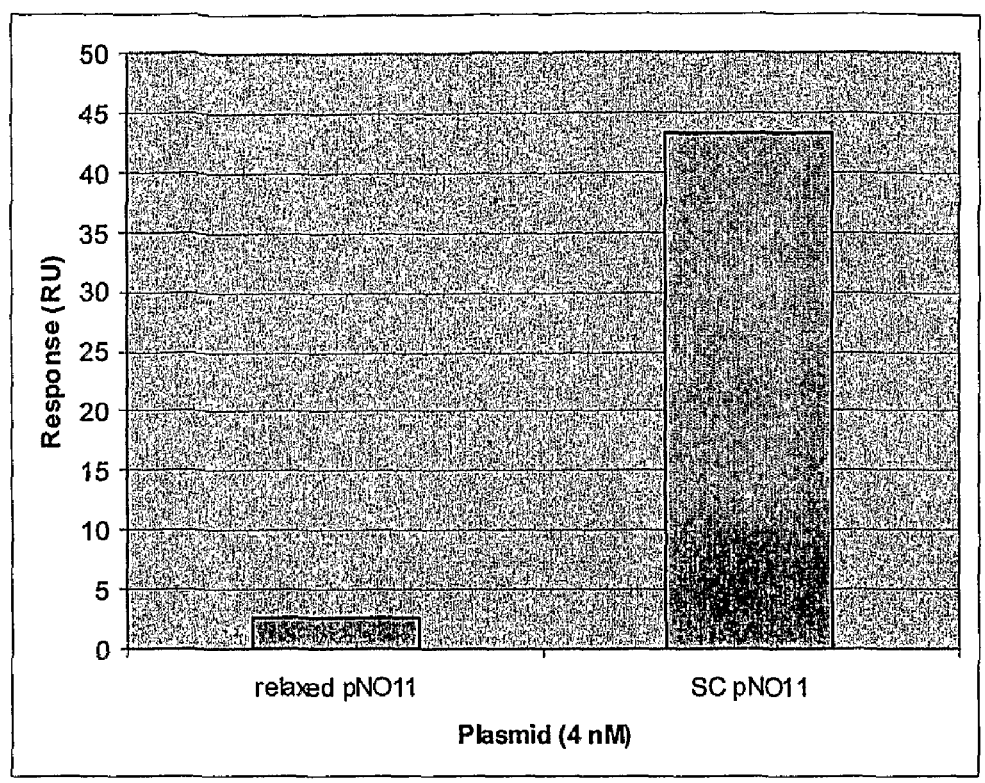

The second plasmid, pNO11, has two triplex-forming inserts, which could potentially form triplexes with TFO1 and TFO2; we found in SPR experiments that pNO11 could be captured by either oligo, although the efficiency of capture by TFO2 was somewhat less than by TFO1 (FIG. 2C,D). In both cases the supercoiled form was captured preferentially to the relaxed form. From these data we were able to conclude that both plasmids, when in a supercoiled form, could be captured by an oligonucleotide immobilised on a chip; the relaxed forms of the plasmids were not efficiently captured. These observations form the basis of the assays for topoisomerases, and other enzymes, based on DNA triplex formation.

Example 3

Figure 3:
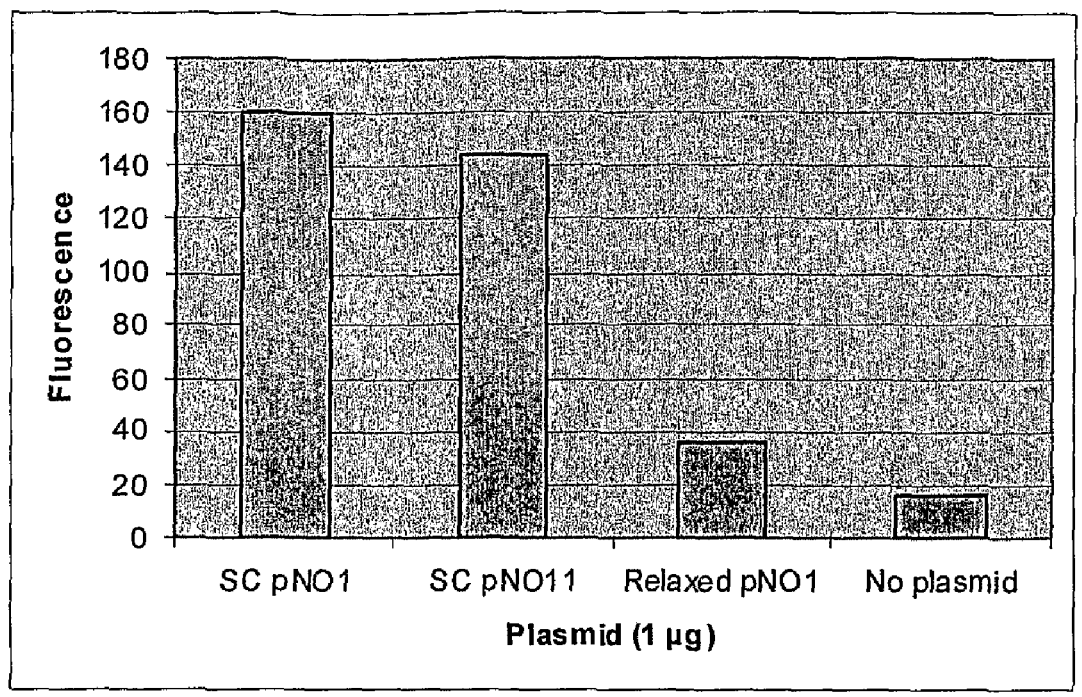
FIG. 3. Capture of plasmids by triplex-forming oligos using fluorescence detection. Plasmids captured by TFO1 in the microplate assay as detected by SYBR staining.

DNA Gyrase Assay According to this Invention—Microplate DNA Gyrase Supercoiling Assay Using a Single Triplex Forming Oligonucleotide:

Having observed plasmid capture by triplex formation using SPR, we transferred these principles to a microplate format. Biotinylated TFO1 was bound to the streptavidin-coated surface of microtitre plates to which plasmids were applied in TF Buffer. Any unbound plasmids were subsequently washed off using the same buffer. The wells were then stained with the nucleic acid stain SYBR Gold and any fluorescence detected using a microplate fluorescence spectrometer. FIG. 3 shows the results of such an experiment using pNO1 and pNO11. As before, the supercoiled form of the plasmids is preferentially captured.

Figure 4A:
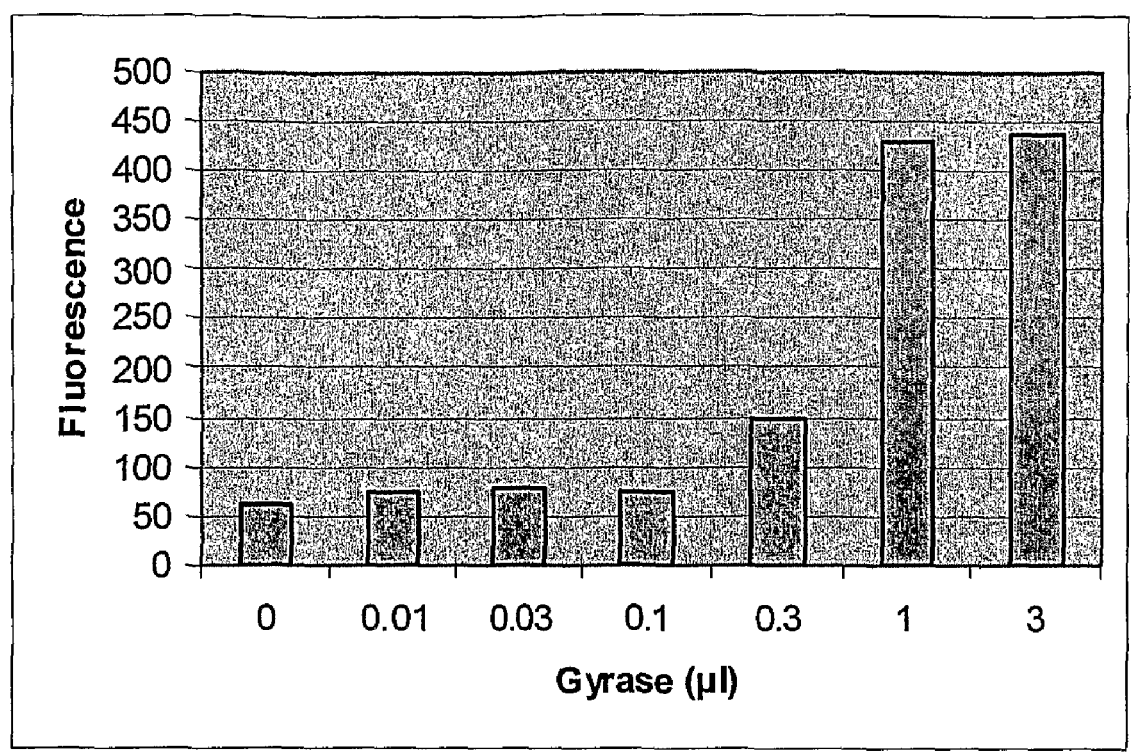
FIG. 4. DNA gyrase supercoiling assay using fluorescence and gel-based assays. Gyrase assay with relaxed pNO1 as a substrate using the indicated amounts of enzyme (1 μl=5 units). Samples were analysed by SYBR fluorescence (A) and gel electrophoresis (B).
Figure 4B:
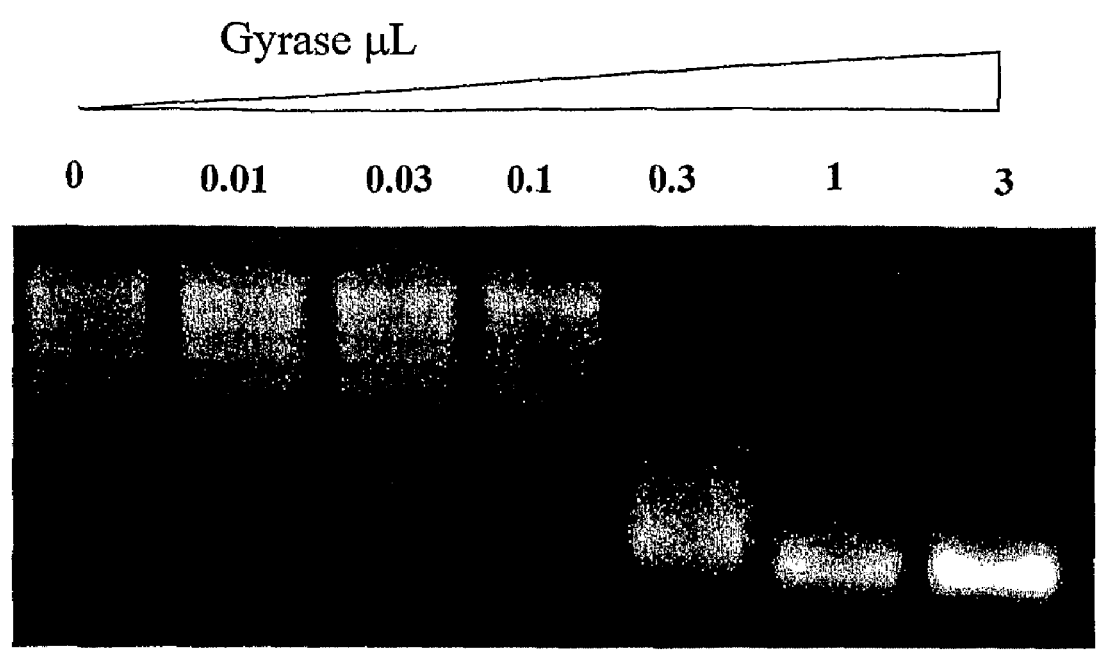
Figure 5A:
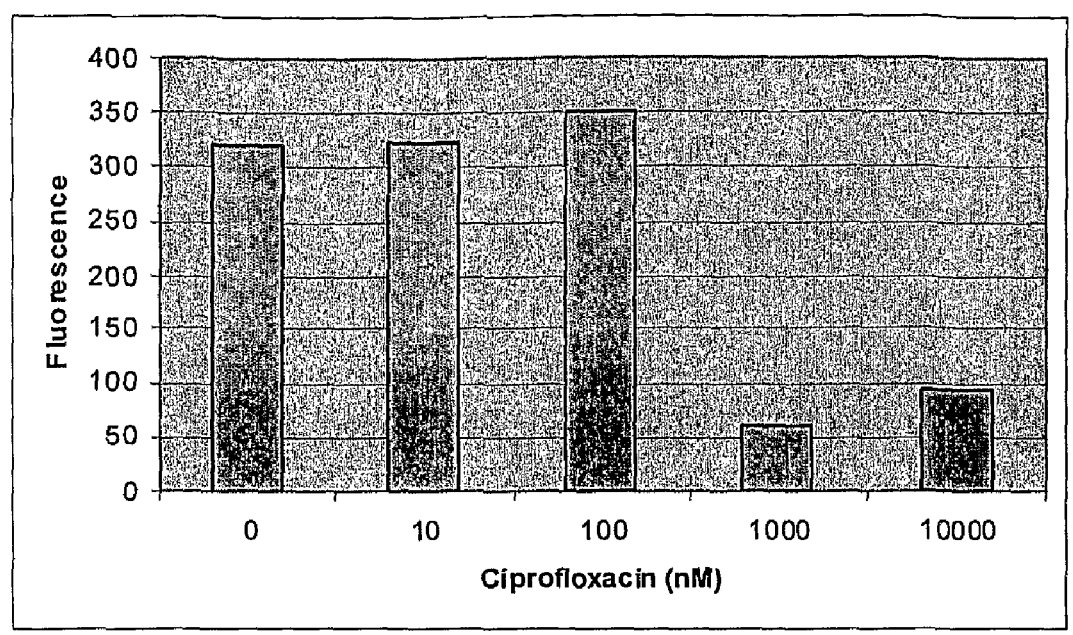
FIG. 5. Effect of ciprofloxacin and novobiocin on DNA gyrase detected by fluorescence and gel-based assays. Gyrase assay (using 5 units of enzyme) with relaxed pNO1 as a substrate in the presence of the indicated amounts of ciprofloxacin (A,B) or novobiocin (C,D). Samples were analysed by SYBR fluorescence (A,C) and gel electrophoresis (B,D).
Figure 5B:
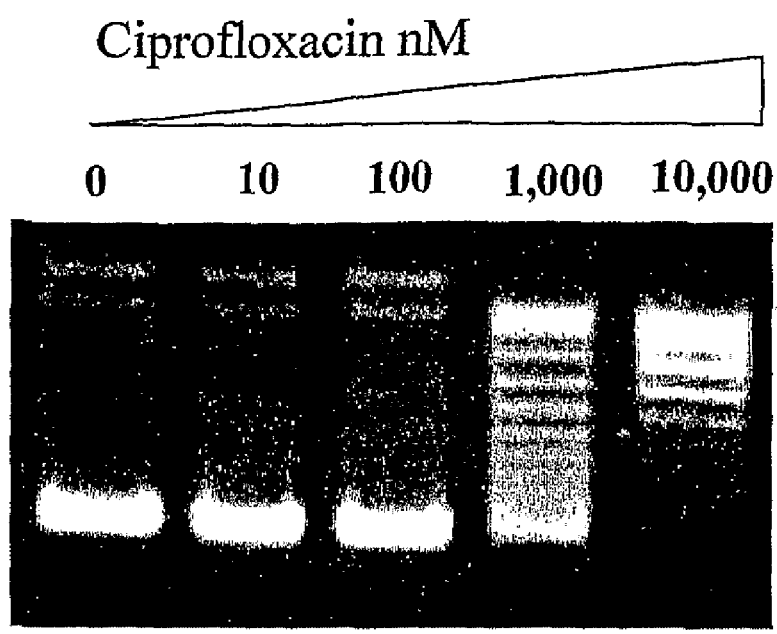
Figure 5C:
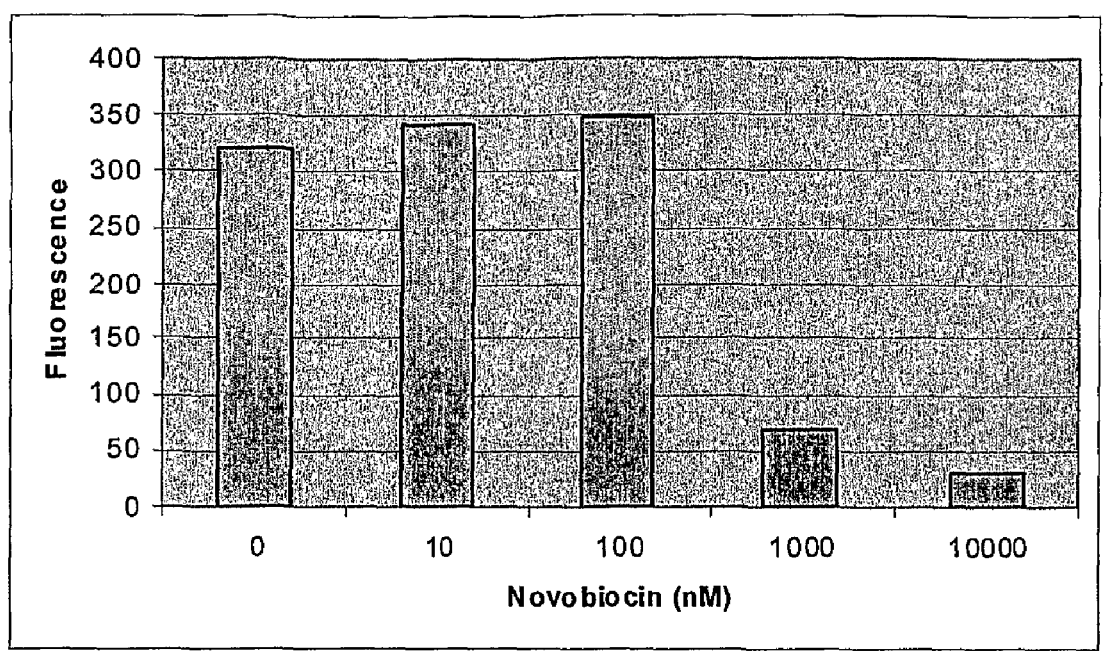
Figure 5D:
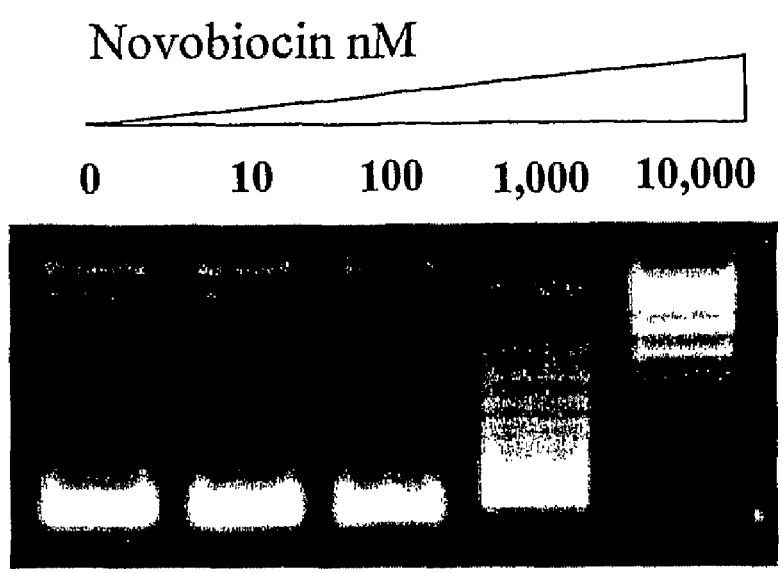
Figure 6A:
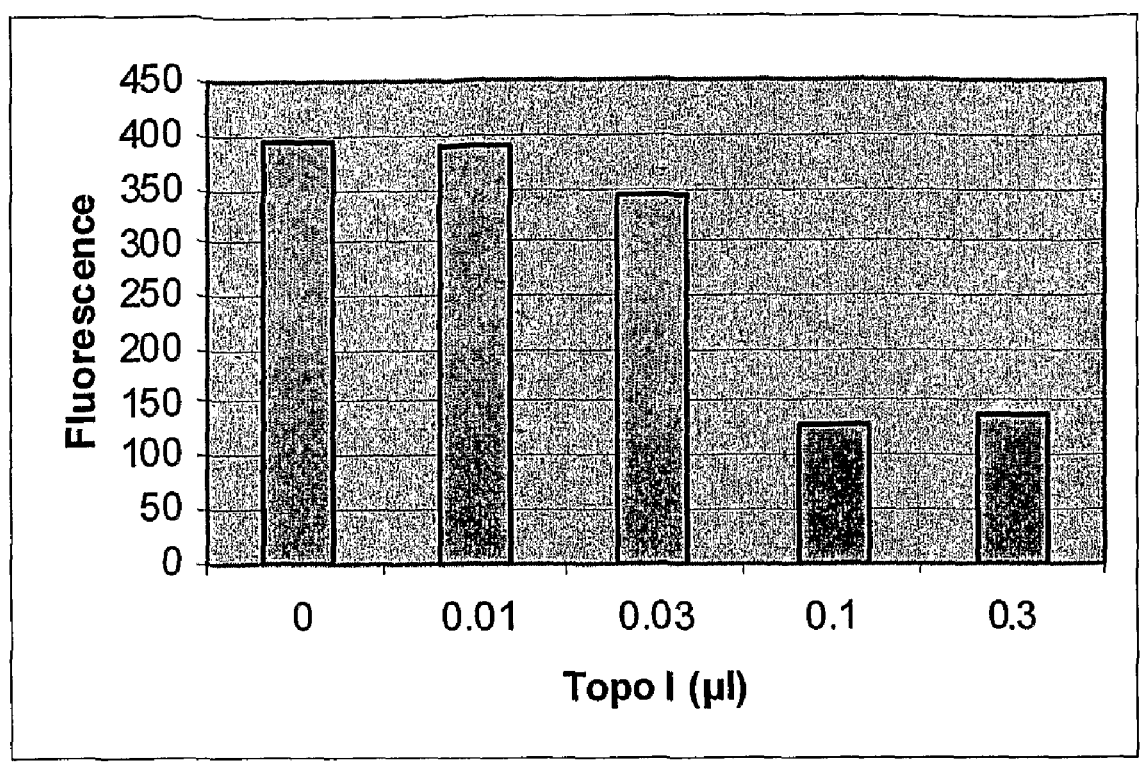
FIG. 6. Topo I and topo IV assays using fluorescence and gel-based assays. Relaxation assay with relaxed pNO1 as a substrate in the presence of the indicated amounts of topo I (A,B) or topo IV (C,D). Samples were analysed by SYBR fluorescence (A,C) and gel electrophoresis (B,D).
Figure 6B:
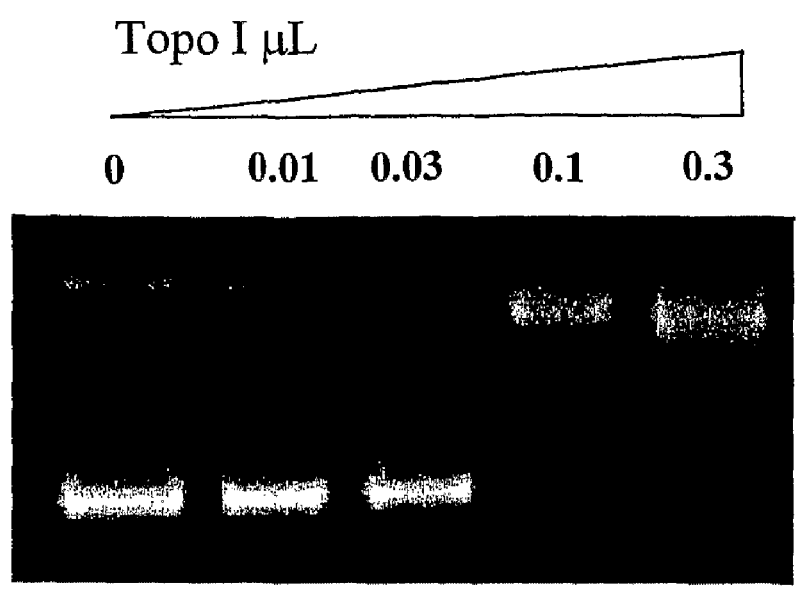
Figure 6C:
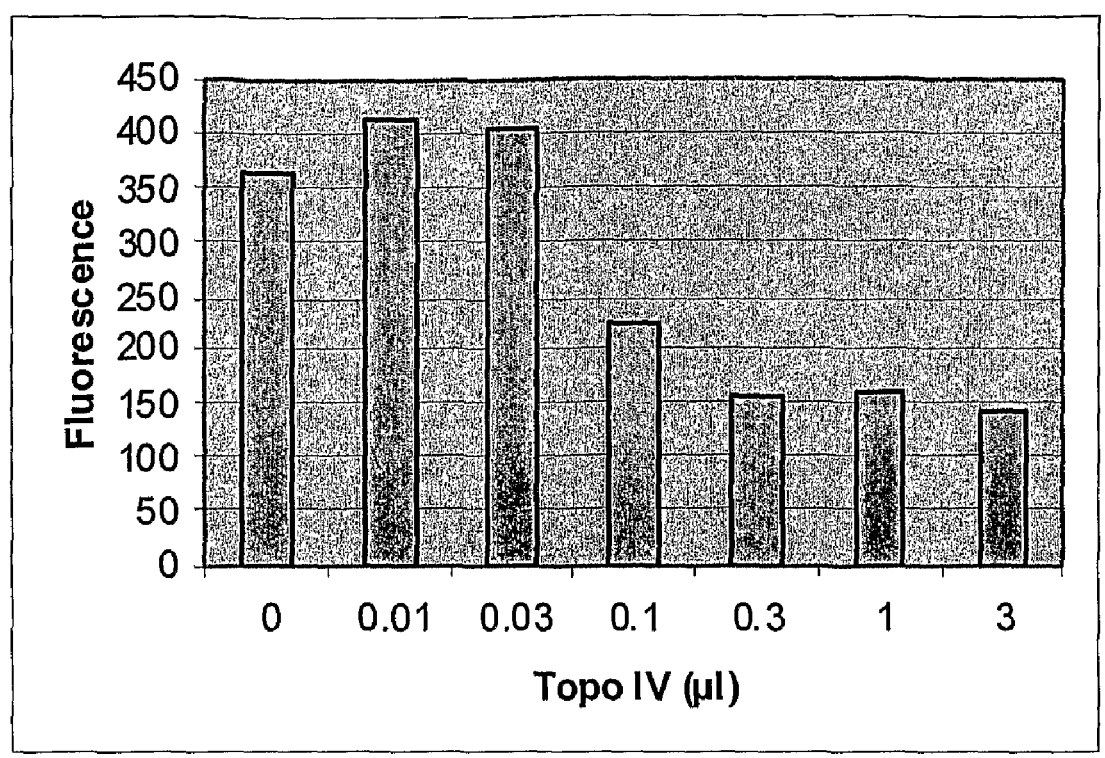
Figure 6D:
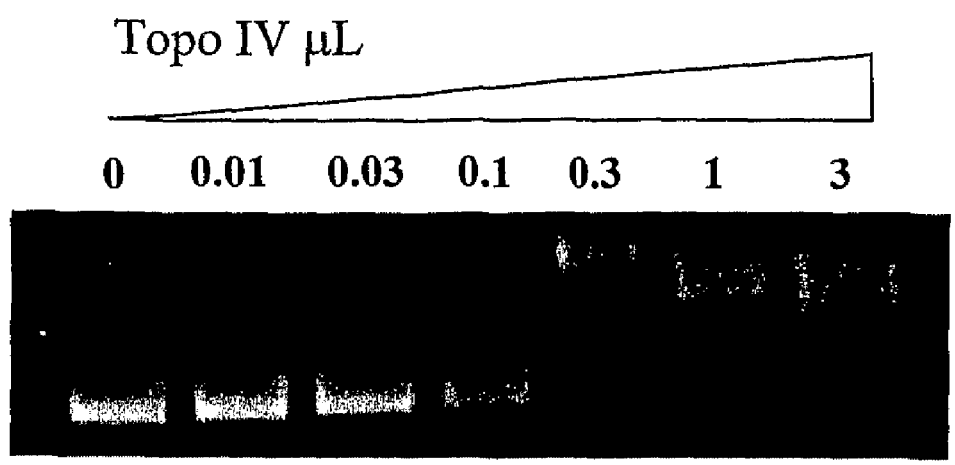

To investigate the utility of this assay for DNA topoisomerases, a DNA gyrase supercoiling assay was carried out in a microplate format using a range of gyrase concentrations; samples were removed from the wells after incubation with gyrase for analysis by gel electrophoresis (FIG. 4). This experiment shows that the conversion of the relaxed DNA substrate to the supercoiled product is readily detected by the fluorescence assay and that the fluorescence results parallel those in the gel assay (FIG. 4).

A key feature of a topoisomerase assay is that it can be utilised to screen for inhibitors. To illustrate this we carried out gyrase supercoiling assays in the presence of varying concentrations of the drugs ciprofloxacin and novobiocin; again samples for analysis by gel electrophoresis were taken in parallel (FIG. 5). The data show that the fluorescence assay mirrors the results in the gel assay and correctly reflects the degree of inhibition by the drugs.

Figure 7:
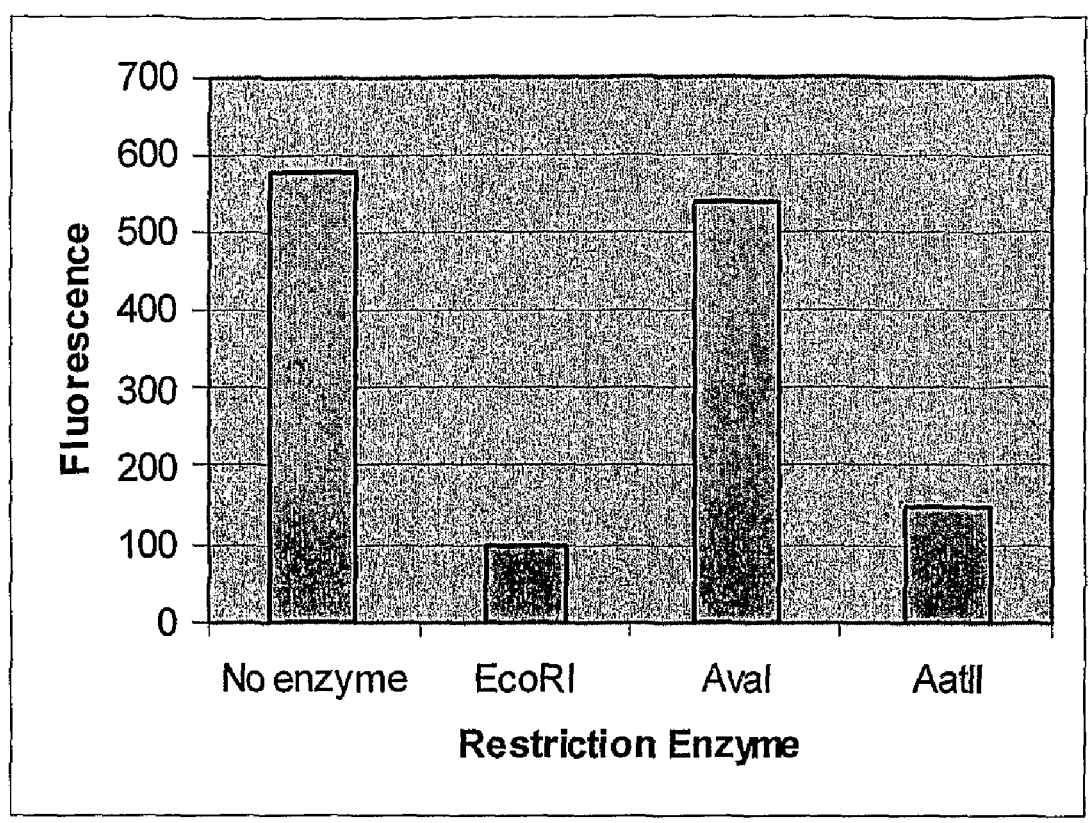
FIG. 7. Restriction enzyme cleavage assayed using fluorescence. Supercoiled plasmid pNO1 was cleaved with the indicated restriction enzymes and samples were analysed by SYBR fluorescence in the microplate assay.

We also carried out relaxation assays using wheat germ topo I and E. coli topo IV (FIG. 6). In this case the substrate (supercoiled DNA) shows high fluorescence and the product (relaxed DNA), low fluorescence. Again the fluorescence assays (FIG. 6A,C) mirror the results in the gel assays (FIG. 6B,D). It is likely that this assay can be adapted for any DNA topoisomerase. Indeed any enzyme that changes the supercoiling of DNA can be assayed. FIG. 7 shows microplate fluorescence assays monitoring the cleavage of pNO1 by restriction enzymes. This plasmid contains sites for EcoRI and AatII but not AvaI; this is reflected by a loss of fluorescence with EcoRI and AatII, but not with AvaI.

Example 4

Figure 8A:
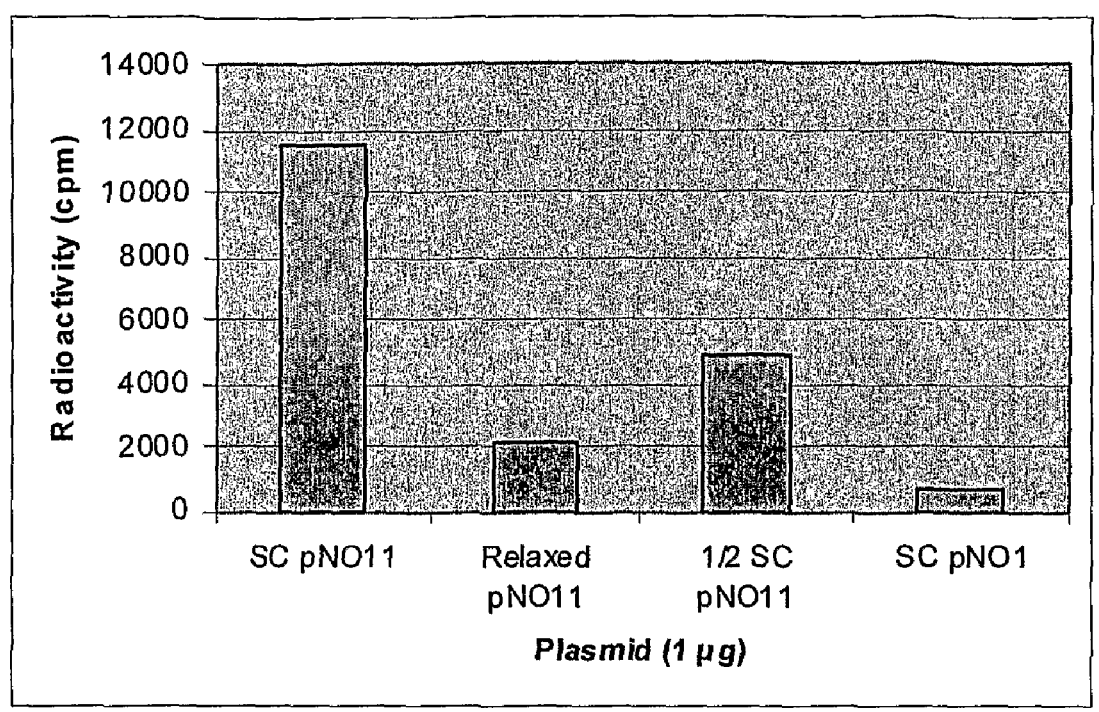
FIG. 8. Plasmid capture and supercoiling assay using the two-triplex method. A, Plasmids captured by TFO1 in the microplate assay and detected by radiolabelled TFO2. B,C, Gyrase assay with relaxed pNO11 as the substrate using the indicated amounts of enzyme (1 μl=5 units). Samples were analysed by binding of radiolabelled TFO2 (B) and gel electrophoresis (C).
Figure 8B:
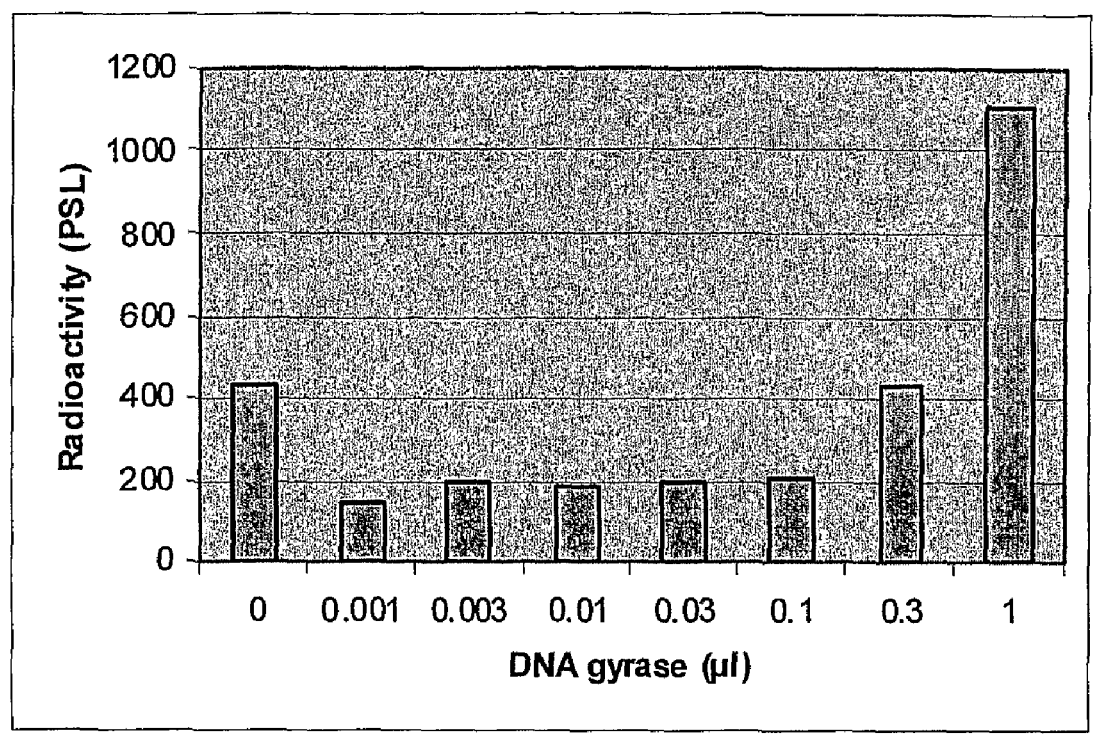
Figure 8C:
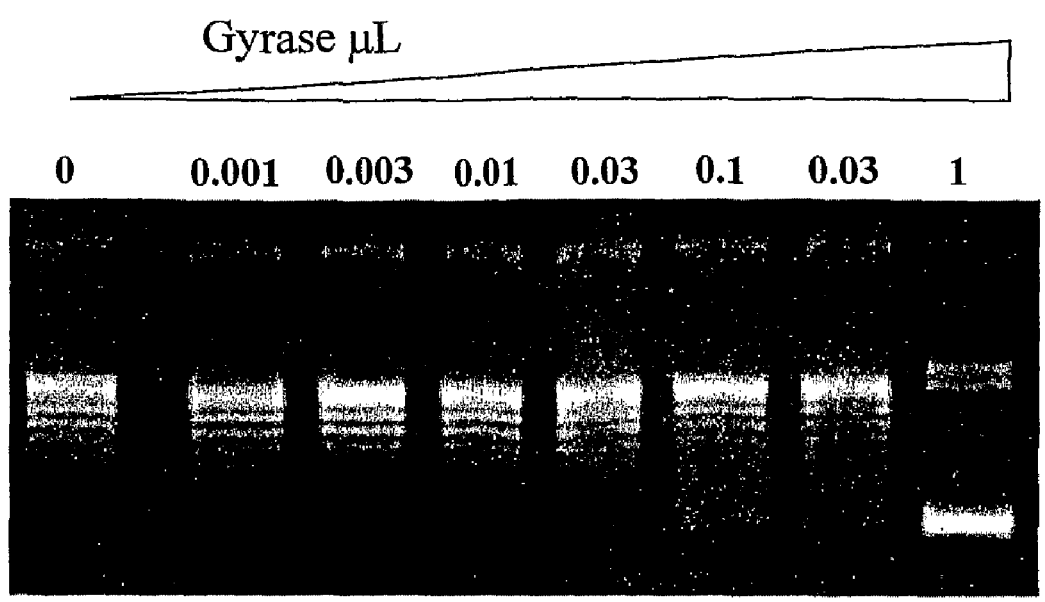

Microplate DNA Gyrase Supercoiling Assay Using Two Triplex Forming Oligonucleotides:

The microplate assay based on two triplex formations has the same principles as described above but requires the formation of a second triplex to give the signal that there is a captured plasmid. In this case we immobilised biotinylated TFO1 onto streptavidin-coated microplate wells and monitored the capture of pNO11. Following capture, the presence of bound plasmid was detected using radiolabelled TFO2. In control experiments we showed that supercoiled pNO11 was captured more efficiently than its relaxed form (FIG. 8A); partially supercoiled pNO11 gave an intermediate signal. We also showed that triplex formation between TFO2 and pNO11 is specific, as supercoiled pNO1 (which does not contain the second triplex sequence) did not give significant signal (data not shown). A DNA gyrase supercoiling assay, similar to that in FIG. 3, was performed in the microplate using this method (FIG. 8B,C). Again the radioactive signal detected reflected the results seen in the gel-based assay.

Example 5

DNA Gyrase SC Assay in Microplate

The method of this invention may be practiced with in accordance with the following detailed disclosure. It will be recognized that the specifics outlined here may be modified without departing from the essential features of the disclosed and claimed method:

Pierce Wash Buffer: TBS, 0.1% BSA, 0.05% Tween-20
TBS: 20 mM Tris.HCl (pH 7.6), 137 mM NaCl
TF Buffer: 50 mM NaOAc pH 5, 50 mM NaCl, 50 mM $MgCl_2$
T10 Buffer: 10 mM Tris.HCl (pH 8), 0.1 mM EDTA
Rehydrate wells with 3×200 µl Wash Buffer.
Immobilise 100 µl 500 nM TFO1 in wells (5 µl 10 µM TFO1 in 95 µl Wash Buffer).
Wash off excess oligo with 3×200 µl Wash Buffer.
Perform SC assay in microplate (total vol: 30 µl, use 1 µg relaxed pNO1).
Add dilution buffer to wells.
Add mastermix to wells.
Add gyrase to wells.
Incubate in SpectraMax at 37° C. for 30 min.
Add 100 µl TF Buffer to wells.
Incubate for 30 mins at room temperature to allow triplex formation.
Wash wells with 3'200 µl TF Buffer to remove unbound plasmid.
Stain wells with 200 µl 1×SYBR Gold for 10-20 mins (20 µl 10×SYBR Gold+180 µl T10 Buffer). Stain in Spectramax drawer.
Read plate using SpectraMax, endpoint read. Ex: 495 nm; Em: 537 nm.

In the following experiments, the following conditions were used:

Each DNA gyrase supercoiling reaction contained 1.0 µg of relaxed pNO1 DNA in a 60 µl volume under the following conditions: 35 mM Tris.HCl (pH 7.5), 24 mM KCl, 4 mM $MgCl_2$, 2 mM DTT, 1.8 mM spermidine, 1 mM ATP, 6.5% (w/v) glycerol and 0.1 mg/ml BSA in addition to DNA gyrase.

30 µl of each reaction was incubated in a well in the microtitre plate for 30 minutes at 37° C. before following the standard assay protocol.

The other 30 µl of each reaction was incubated at 37° C. for 30 minutes in Eppendorf tubes, the reactions stopped by the addition of 30 µl chloroform/iso-amyl alcohol (24:1) and 8 µl Stop Dye (40% sucrose, 100 mM Tris.HCl (pH 7.5), 100 mM EDTA, 0.5 µg/ml bromophenol blue), before being loaded on a 0.8% TAE (40 mM Tris.acetate, 2 mM EDTA) gel. Bands were visualised by ethidium staining for 10 minutes and gels analysed by gel documentation equipment (Syngene, Cambridge, UK). In each case the reaction was followed by analysing the intensity of the supercoiled band.

Figure 9:
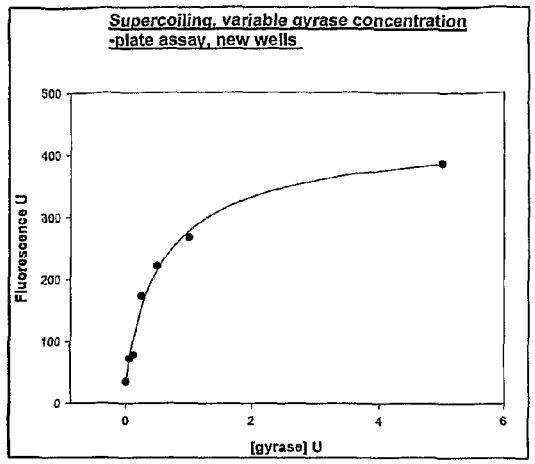
FIG. 9: Graphs 1-4: effect of varying amounts of gyrase; comparison of assay performed on a gel with that in the plate assay using new or re-used wells.
Figure 9:
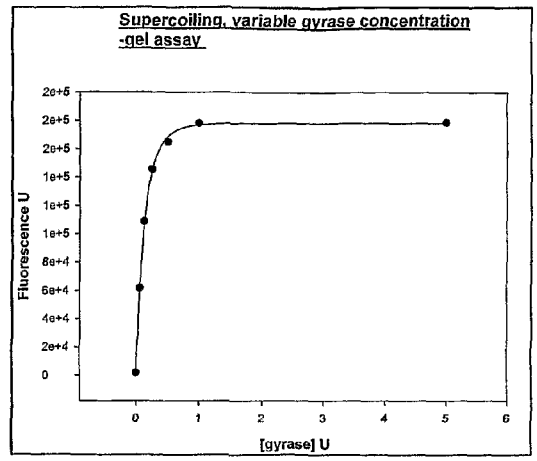
Figure 9:
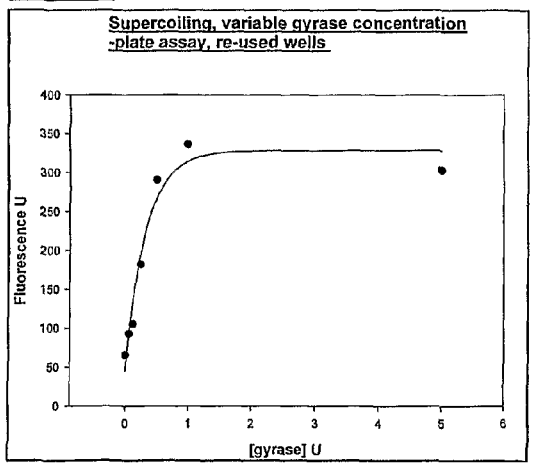
Figure 9:
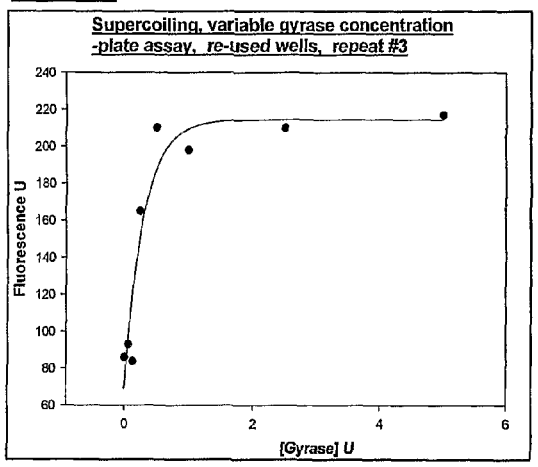

As shown in FIG. 9 (Graphs 1 to 4), when the supercoiling of relaxed pNO1 by varying concentrations of gyrase was followed using the plate and gel based assays, similar results were obtained for both assays.

Additionally, this Figure shows that it is possible to re-use the wells without loss of sensitivity. This further improves the economics of the invention, particularly in respect of high throughput screening. It was found that it is possible to re-use the wells for supercoiling reactions at least 4 times (results not shown).

It was also possible to re-use wells after they had been used to test inhibitors. This was confirmed by comparing supercoiling reactions in new wells and those which had previously been used for testing the inhibitory activity of simocyclinone D8 on gyrase (results not shown).

Figure 10:
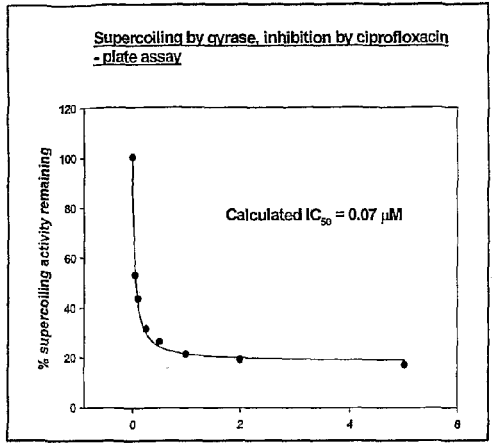
FIG. 10. Graphs 5-10: inhibition of gyrase supercoiling activity by various inhibitors; comparison of assay performed on a gel with that in the plate assay.
Figure 10:
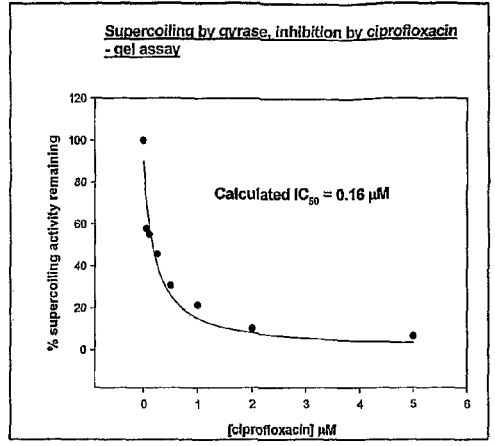
Figure 10:
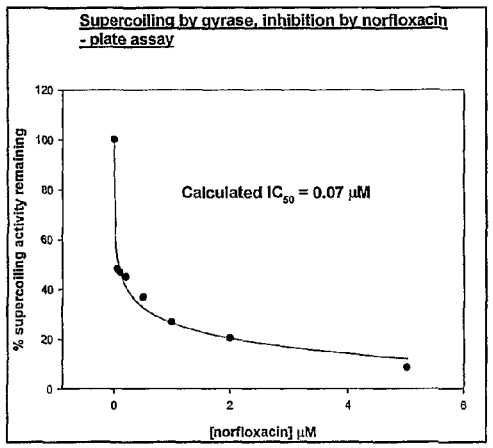
Figure 10:
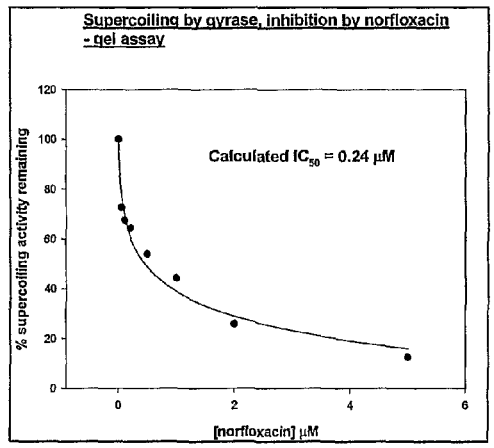
Figure 10:
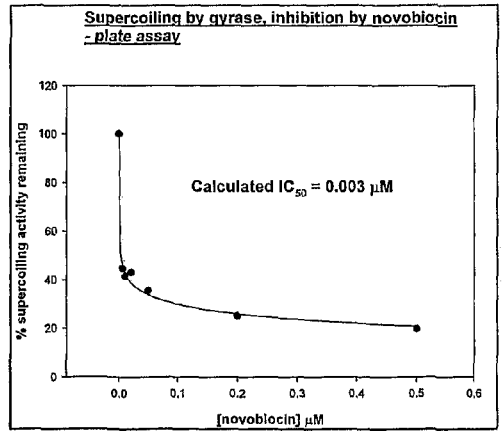
Figure 10:
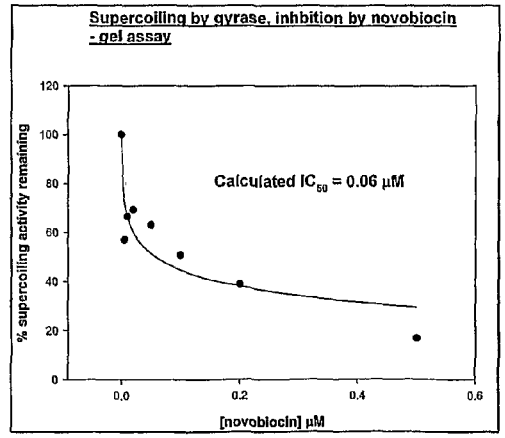

FIG. 10 (Graphs 5 to 10) shows a comparison of supercoiling activity of gyrase by inhibitors ciprofloxacin, norfloxacin and novobiocin. Similar results were obtained with plate and gel based assays.

$IC_{50}$ values were obtained using SigmaPlot (version 8.0) software from plots of amount of supercoiled DNA, determined from scanned gels or direct from plate assays, versus enzyme or inhibitor concentration. The calculated $IC_{50}$ values were lower for the plate assay than the gel based assay. However this matches what would theoretically be expected, since in the gel assay only a proportion of the supercoiled species are resolved on the gel, and the IC50 is in turn calculated based on achieving 50% inhibition of that proportion (which will reflect >50% inhibition of the overall species). Thus the gel assay would be expected to overestimate the true IC50 value.

Example 6

Topoisomerase relaxation reactions were performed in an identical manner to that used in Example 5, but contained 1.0 µl of supercoiled pNO1 DNA in a 60 µl reaction volume containing 40 mM HEPES-KOH (pH 7.6), 100 mM potassium glutamate, 10 mM magnesium acetate, 10 mM DTT, 4 µg/ml tRNA, 2 mM ATP and 50 µg/ml BSA.

Figure 11:
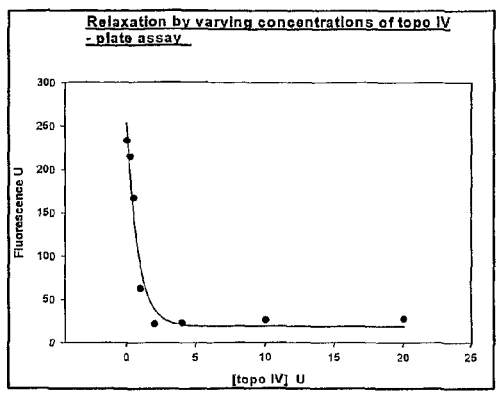
FIG. 11. Graphs 11-12: effect of varying amounts of topoisomerase IV on relaxation of substrate; comparison of assay performed on a gel with that in the plate assay FIG. 12. Graphs 13-20: inhibition of topoisomerase IV relaxation activity by various inhibitors; comparison of assay performed on a gel with that in the plate assay.
Figure 11:
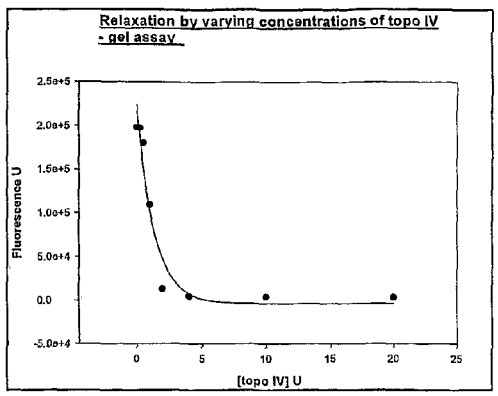

The relaxation of supercoiled pNO1 by varying concentrations of topoisomerase IV was followed using the plate and gel based assays and the results compared in FIG. 11 (Graphs 11-12). Similar results were obtained.

Figure 12:
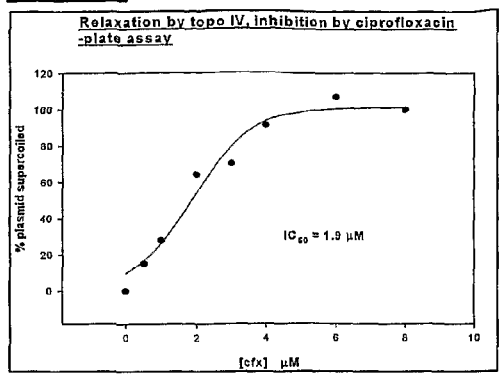
Figure 12:
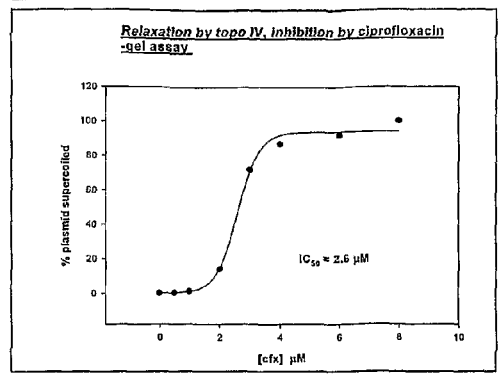
Figure 12:
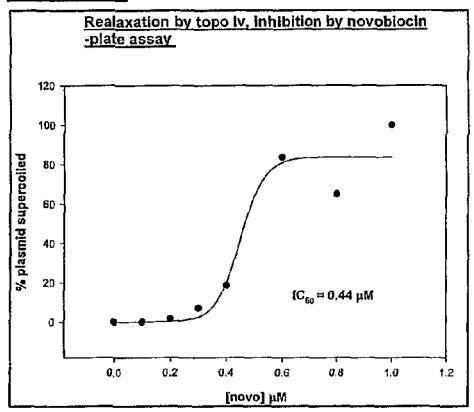
Figure 12:
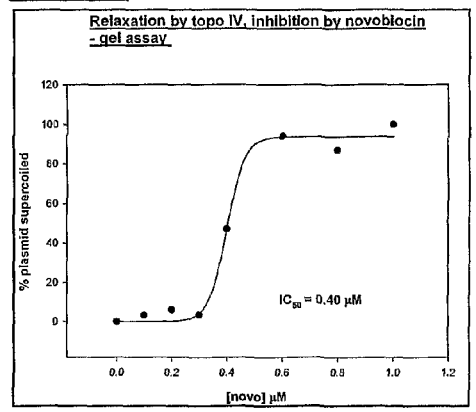

FIG. 12 (Graphs 13-20) compares inhibition of relaxation activity of topoisomerase IV by inhibitors ciprofloxacin, novobiocin, nalidixic acid and clorbiocin. Similar results were obtained with both gel and plate assays.

Example 7

Human topoisomerases I and 11 are potential anti-cancer targets.

Figure 13:
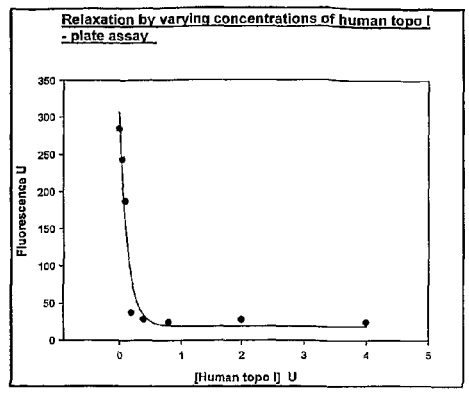
FIG. 13. Graphs 21-22: effect of varying amounts of human topoisomerase I; comparison of assay performed on a gel with that in the plate assay.
Figure 13:
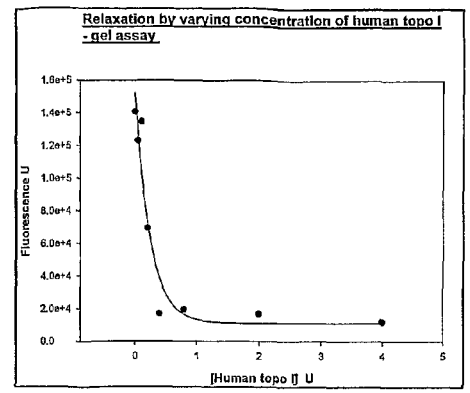

The relaxation of negatively supercoiled pNO1 by varying amounts of human topoisomerase I was compared in gel and plate assays and the results compared in FIG. 13 (Graphs 21-22). Similar results were obtained.

Figure 14:
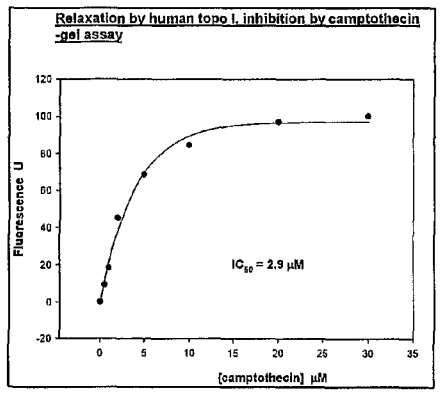
FIG. 14. Graphs 23-24: inhibition of human topoisomerase I relaxation activity by camptothecin; comparison of assay performed on a gel with that in the plate assay.
Figure 14:
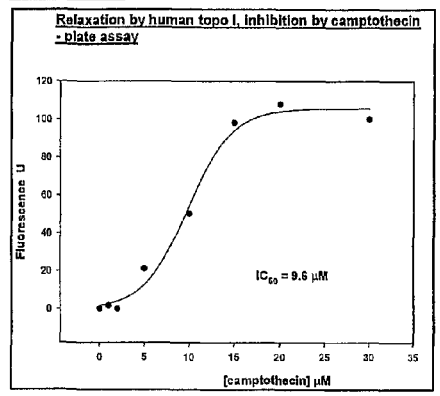

FIG. 14 (Graphs 23-24) compares inhibition of relaxation activity of human topoisomerase I by the inhibitor camptothecin in the gel and plate assays. Similar results were obtained.

Figure 15:
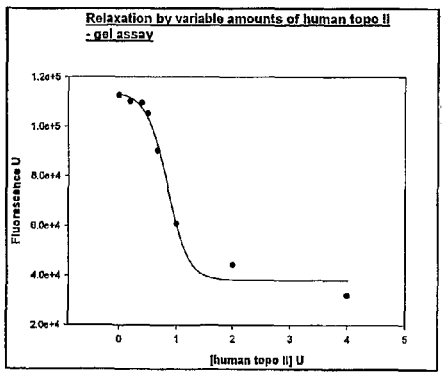
FIG. 15. Graphs 25-26: effect of varying amounts of human topoisomerase 11; comparison of assay performed on a gel with that in the plate assay.
Figure 15:
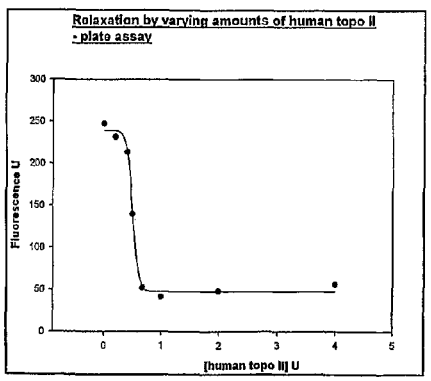

The relaxation of negatively supercoiled pNO1 by varying amounts of human topoisomerase II was compared in gel and plate assays and the results compared in FIG. 15 (Graphs 25-26). Similar results were obtained.

Summary of Results—Examples 5-7

All results are given in µM

| Compound | DNA gyrase Supercoiling $IC_{50}$ | | | Topo IV Relaxation $IC_{50}$ | | |
|---|---|---|---|---|---|---|
| | Plate assay | Gel assay | Expected | Plate assay | Gel assay | Expected |
| Ciprofloxacin | 0.07 | 0.16 | 1.1[a] | 1.9 | 2.6 | 2.5-5.0 |
| Norfloxacin | 0.07 | 0.24 | 4.8[a] | — | — | — |
| Novobiocin | 0.003 | 0.06 | 0.05 | 0.44 | 0.4 | 0.3-0.5 |
| Naladixic acid | — | — | — | 88.4 | 36.3 | 270 |
| Chlorbiocin | — | — | — | 0.32 | 0.14 | — |

[a]Barnard, F. M. and Maxwell, A., (2001). Antimicrobial Agents and Chemotherapy 45(7): 1994-2000

| Compound | Human topoisomerase I $IC_{50}$ (µM) | | |
|---|---|---|---|
| | Plate assay | Gel assay | Expected |
| Camptothecin | 9.6 | 2.9 | 5-25[a] |

[a]Okada et al., (1987). PNAS (USA) 84: 5565-5569

Example 8

Development of a Single-Catenane Substrate to Follow Decatenation Reactions in the Plate assay Decatenation reactions are usually performed in gel based assays using the substrate kDNA, a large complex of many plasmid minicircles (Flatman, R. H., Howells, A. J., Heide, L., Fiedler, H-P., and Maxwell, A. (2005) Antimicrobial Agents and Chemotherapy 49(3): 1093-1100.)

As an alternative, the present invention provides a single-catenane substrate comprising two interlinked plasmids, one of which can be captured using triplex forming sequences, while the other is released by the decatenation reaction.

Preferably the smaller plasmid contains the triplex-forming sequence. Decatenation by the target enzyme leads to only the small circle being retained in the microtitre plate and the reaction is followed, as with the supercoiling/relaxation assay, by staining the retained DNA. Sensitivity is maximised by using circles having a large difference in size. Optionally the smaller plasmid is treated with an excess of gyrase following decatenation to maximise supercoiling prior to capture.

The single-catenane substrate may be prepared by treating a plasmid containing two internal resolution sites with the enzyme resolvase. This can be used, for example, to assay topoisomerase IV and human topoisomerase II.

The invention claimed is:

1. A method of assessing or measuring the ability of an enzyme to modify the supercoil topology of a target nucleic acid, the method comprising the steps of:
   (a) providing a solid support to which a capture nucleic acid is or can be immobilised,
   which capture nucleic acid is capable of binding the target nucleic acid in a manner that is proportional to the supercoil topology of said target nucleic acid;
   (b) incubating a test mixture comprising (i) the enzyme, (ii) the target nucleic acid, (iii) capture nucleic acid, in the presence of (iv) said solid support,
   such that supercoiled target nucleic acid bound by the capture nucleic acid is immobilised to the solid support, and
   (c) determining the amount of target nucleic acid bound by said capture nucleic acid in step (b),
   wherein the target nucleic acid comprises at least one region or insert capable of forming a triplex with the capture nucleic acid.

2. The method of claim 1 wherein the solid support and capture nucleic acid are combined prior to formation of the test mixture in step (b) and the solid support is washed prior to step (b) to remove excess capture nucleic acid.

3. The method of claim 1 wherein the capture nucleic acid becomes immobilised to the solid support in step (b).

4. The method of claim 1 wherein step (b) is carried out:
   (i) at a first pH selected to be optimal for the activity of the enzyme, followed by (ii) a second pH selected to be optimal for binding between the capture nucleic acid and target nucleic acid.

5. The method of claim 1 wherein the amount of bound nucleic acid is determined by use of a labeling moiety including a detectable label.

6. The method of claim 5 wherein the labeling moiety is present on or in the target nucleic acid.

7. The method of claim 5 wherein the labeling moiety is bound to the target nucleic acid during step (b), and step (c) is preceded by a wash step to remove unbound detectable label.

8. The method of claim 7 wherein the labeling moiety is a nucleic acid capable of forming a triplex with supercoiled target nucleic acid.

9. The method of claim 1 wherein the capture nucleic acid is immobilised via an immobilisation tag comprised within the capture nucleic acid to form an immobilisation moiety.

10. The method of claim 1 wherein said capture nucleic acid contains a contiguous sequence of at least 5, 7 or 10 alternating pyrimidine repeats.

11. The method of claim 1 wherein said capture nucleic acid sequence is selected from TF01 (SEQ ID NO: 1) or TFO2 (SEQ ID NO: 2), or is at least 80% identical thereto.

12. The method of claim 1 wherein the determination step is performed with the target nucleic acid bound to the solid support.

13. The method of claim 1 wherein the bound target nucleic acid is released from the solid support and the amount is subsequently determined.

14. The method of claim 1 wherein said enzyme which modifies the topology of target nucleic acid is a topoisomerase, a gyrase, a nuclease or a restriction enzyme.

15. The method of claim 1 wherein said target nucleic acid is selected from the group consisting of a covalently closed circular plasmid DNA and a concatenated closed circular plasmid DNA.

16. The method of claim 1 wherein said region or insert capable of forming a triplex with the capture nucleic acid contains a contiguous sequence of at least 5, 7 or 10 alternating pyrimidine or purine repeats.

17. The method of claim 1 wherein said region or insert capable of forming a triplex with the capture nucleic acid is selected from any of TF01W (SEQ ID NO: 3); TF01C (SEQ ID NO: 4); TFO2W (SEQ ID NO: 5); TFO2C (SEQ ID NO: 6), or is at least 80% identical thereto.

18. A method of assessing or measuring the modulating activity of a potential modulator on the ability of an enzyme to modify the supercoil topology of a target nucleic acid, the method comprising the steps of:
(a) providing a solid support to which a capture nucleic acid is or can be immobilised,
which capture nucleic acid is capable of binding the target nucleic acid in a manner that is proportional to the supercoil topology of said target nucleic acid;
(b) incubating a test mixture comprising (i) the enzyme, (ii) the target nucleic acid, (iii) capture nucleic acid, in the presence of (iv) said solid support and (v) the potential modulator,
such that supercoiled target nucleic acid bound by the capture nucleic acid is immobilised to the solid support, and
(c) determining the amount of target nucleic acid bound by said capture nucleic acid in step (b),
wherein the target nucleic acid comprises at least one region or insert capable of forming a triplex with the capture nucleic acid.

19. The method of claim 18 wherein the value resulting from the determination at step (c) is compared with the value in the absence of the potential modulator, and the modulating activity is correlated with the result of the comparison.

20. A method of measuring the activity of a topoisomerase or gyrase which modifies the supercoil topology of a target nucleic acid in the presence of a potential topoisomerase or gyrase activity modulator, the method comprising:
(a) incubating a test mixture comprising: (i) said topoisomerase or gyrase, (ii) a target nucleic acid optionally comprising a labeling moiety, and (iii) a potential activity modulator;
(b) combining the test mixture and (iv) an immobilization moiety which comprises an immobilization tag and a capture nucleic acid that binds the target nucleic acid in a manner that is proportional to the supercoil topology of said target nucleic acid;
wherein said immobilization tag is bound to a solid support, thereby binding to said solid support said immobilization moiety, and any target nucleic acid bound to said immobilization moiety via said capture nucleic acid;
(c) washing the solid support to remove target nucleic acid which is not bound to the immobilization moiety;
(d) contacting the solid support-bound immobilization moiety, and any target nucleic acid bound to said immobilization moiety via said capture nucleic acid, with (vi) a labeling moiety, unless such labeling moiety is comprised by said target nucleic acid;
(e) washing away any unbound labeling moiety, if necessary; and
(f) determining whether and to what degree said potential activity modulator modulates the activity of said topoisomerase or gyrase by measuring the degree of target nucleic acid binding to said immobilization moiety,
wherein the tarp et nucleic acid corn rises at least one region or insert capable of forming a triplex with the capture nucleic acid.

21. The method of claim 20 wherein said immobilization moiety comprises an oligonucleotide capture nucleic acid comprising a target nucleic acid binding moiety which binds to said target nucleic acid via triplex formation.

22. The method of claim 20 wherein said target nucleic acid comprises a detectable label.

23. The method of claim 22 wherein said detectable label is a fluorescent dye or radiolabel.

24. The method of claim 20 wherein said labeling moiety comprises an oligonucleotide comprising a detectable label and wherein said oligonucleotide of the labeling moiety binds to said target nucleic acid through triplex formation.

25. The method of claim 20 wherein incubating the test mixture comprising the potential activity modulator results in a greater amount of supercoiling or a reduced amount of supercoiling of said target nucleic acid than in a mixture which does not comprise said potential activity modulator.

26. The method of claim 20 wherein the potential modulator is an inhibitor.

27. A method of assessing or measuring the ability of an enzyme to modify the topology of a target nucleic acid by decatenation thereof, the method comprising the steps of:
(a) providing a solid support to which a capture nucleic acid is or can be immobilised, wherein the target nucleic acid is a concatenated closed circular plasmid DNA, and wherein the capture nucleic acid is capable of binding one of the circles of the target nucleic acid in a manner that is proportional to its supercoil topology;
(b) incubating a test mixture comprising (i) the enzyme, (ii) the target nucleic acid, (iii) capture nucleic acid, in the presence of (iv) said solid support, such that supercoiled target nucleic acid bound by the capture nucleic acid is immobilised to the solid support, and
(c) determining the amount of target nucleic acid bound by said capture nucleic acid in step (b),
wherein the target nucleic acid comprises at least one region or insert capable of forming a triplex with the capture nucleic acid.

* * * * *

UNITED STATES PATENT AND TRADEMARK OFFICE
CERTIFICATE OF CORRECTION

Page 1 of 1

PATENT NO.        : 7,838,230 B2
APPLICATION NO.   : 11/718978
DATED             : November 23, 2010
INVENTOR(S)       : Anthony Maxwell It is certified that error appears in the above-identified patent and that said Letters Patent is hereby corrected as shown below:

| Col. No. | Line(s) | |
|---|---|---|
| 22 | 33 | Replace "the tarp et nucleic acid corn rises" with --the target nucleic acid comprises-- |

Signed and Sealed this
First Day of February, 2011

David J. Kappos
*Director of the United States Patent and Trademark Office*